(12) United States Patent
Sugihara et al.

(10) Patent No.: US 6,890,762 B1
(45) Date of Patent: May 10, 2005

(54) METHOD FOR MEASURING PHYSIOCOCHEMICAL PROPERTIES OF TISSUES OF CELLS, METHOD FOR EXAMINING CHEMICALS, AND APPARATUS THEREFOR

(75) Inventors: Hirokazu Sugihara, Osaka (JP); Yasushi Kobayashi, Kyoto (JP); Hiroaki Oka, Osaka (JP); Ryuta Ogawa, Osaka (JP); Makoto Taketani, Kyoto (JP)

(73) Assignee: Matsushita Technical Information Services Co., Ltd., Kadoma (JP)

( * ) Notice: Subject to any disclaimer, the term of this patent is extended or adjusted under 35 U.S.C. 154(b) by 0 days.

(21) Appl. No.: 08/913,811

(22) PCT Filed: Jan. 24, 1997

(86) PCT No.: PCT/JP97/00153

§ 371 (c)(1),
(2), (4) Date: Sep. 24, 1997

(87) PCT Pub. No.: WO97/27318

PCT Pub. Date: Jul. 31, 1997

(30) Foreign Application Priority Data

Jan. 24, 1996 (JP) .............................................. 8-009857

(51) Int. Cl.[7] ...................... G01N 33/567; G01N 33/53; G01N 33/48; C12Q 1/04; C12N 27/00
(52) U.S. Cl. ........................... 436/503; 436/63; 436/28; 436/806; 436/807; 422/82.01; 435/34
(58) Field of Search ........................... 436/28, 63, 806, 436/807, 503; 435/34; 422/82.01

(56) References Cited

U.S. PATENT DOCUMENTS

| | | | |
|---|---|---|---|
| 4,288,544 A | * | 9/1981 | Suzuki et al. |
| 5,187,096 A | | 2/1993 | Giaever et al. |
| 5,278,048 A | | 1/1994 | Parce et al. |
| 5,563,067 A | * | 10/1996 | Sugihara et al. |

FOREIGN PATENT DOCUMENTS

| | | |
|---|---|---|
| EP | 0585933 | 3/1994 |
| EP | 0 689 051 A2 A3 | 12/1995 |
| GB | 1 514 046 | 8/1976 |
| JP | 52-31825 | 3/1977 |
| JP | 03-265814 | 11/1991 |
| JP | 6-78889 | 3/1994 |
| JP | 06-296595 | 10/1994 |
| WO | WO 90/11371 | 10/1990 |
| WO | WO 91/15595 A1 | 10/1991 |
| WO | WO 91/17240 | 11/1991 |
| WO | WO 92/15700 | 9/1992 |

OTHER PUBLICATIONS

Nisch et al; Biosensors and Bioelectronics ; 9, 737–741, 1994.*
Nicander et al 1995 (British Journal of Dermatology, 132; 718–724), 1995.*
Novak et al., "Recording from the *Aplysia* abdominal ganglion with a planar microelectrode array" *IEEE Trans. Biomed. Eng.* (1986) BME–33(2): 196–202.
Nisch et al., "A thin film microelectrode array for monitoring extracellular neuronal activity in vitro" *Biosens. Bioelect.* (1994) 9: 737–741.
Gross et al., "Recording of spontaneous activity with photoetched microelectrode surfaces from mouse spinal neurons in culture" *J. Neurosci. Meth.* (1982) 5: 13–22.
Yamamoto, "In vitro synaptic activity" *Protein, nucleic acid and enzyme* (1977) 22(6):502–505 (Partial English translation included).
Yamamoto, "Electrical activity of brain sentor" *Protein, nucleic acid and enzyme* (1984) 29(12):1205–1211 (Partial English translation included).
Suematsu et al., "α receptor" *Protein, nucleic acid and enzyme* (1984) 29(12):1338–1352 (Partial English translation included).
Kuroda, "Adenosine/ATP receptor in nervous system and physiologic funcion" *Protein, nucleic acid and enzyme* (1984) 29(12):1405–1423 (Partial English translation included).
Yamamoto, "Electrophysiological experiment using brain section" *Science of Human Body* (1972) 23(3):143–150 (Partial English translation included).

(Continued)

*Primary Examiner*—Lynette R. F. Smith
*Assistant Examiner*—Padma Baskar
(74) *Attorney, Agent, or Firm*—Morrison & Foerster LLP

(57) ABSTRACT

A method of measuring the physical and chemical properties of tissue or cells and a device for the same is provided, with which the physical and chemical environment of the tissue or cells can be changed arbitrarily corresponding to experimental necessities. The device comprises a system 40 for keeping the physical and chemical environment surrounding the biological tissue or cells constant, a system 50 for arbitrarily changing the physical and chemical environment, observation systems 10 and 20 for observing the physical and chemical properties of the tissue or cells, and a system 30 for comparing the change of the physical and chemical properties of the tissue or cells before and after changing the physical and chemical environment. The observation system 10 is a potential measurement device for measuring the electrophysiological properties of the tissue or cells. This device comprises an integrated cell placement device 1 provided with a plurality of microelectrodes 11 on a substrate, a cell placement portion 6 for placing the tissue or cells on the microelectrodes 11, and a wiring pattern 12 for applying an electrical signal to the microelectrodes 11 and extracting an electrical signal from the microelectrodes 11.

3 Claims, 15 Drawing Sheets

OTHER PUBLICATIONS

Yamamoto, "Recent knowledge obtained by using a brain section sample" *Science of Human Body* (1981) *32*(5):425–429 (Partial English translation included).

Yamamoto et al., "Black widow spider venom: excitatory action on hippochampal neurons" *Brain Res.* (1982) *244*(2):382–386.

Gäehwiler et al., "Multiple actions of acetylcholine on ippocampal pyramid cells in organotypic explant cultures" *Neuroscience* (1982) *7*(5):1243–1256.

Gonzalés et al., "Cell and explant culture of olfactory chemoreceptor cells" *J. Neurosci.* (1985) *14*(2):77–90.

Hazeki et al. dification by Islet–activating protein of receptor–mediated regulation of cyclic AMP accumulation in isolated rat heart cells *J. Biol. Chem.* (1981) 256(6):2856–2862.

Hofer, E. et al., (May 1994). "Measuring Activation Patterns of the Heart at a Microscopic Size Scale With Thin–Film Sensors," *J. Physiol.* 266(5 Pt 2):H2136–2145.

* cited by examiner

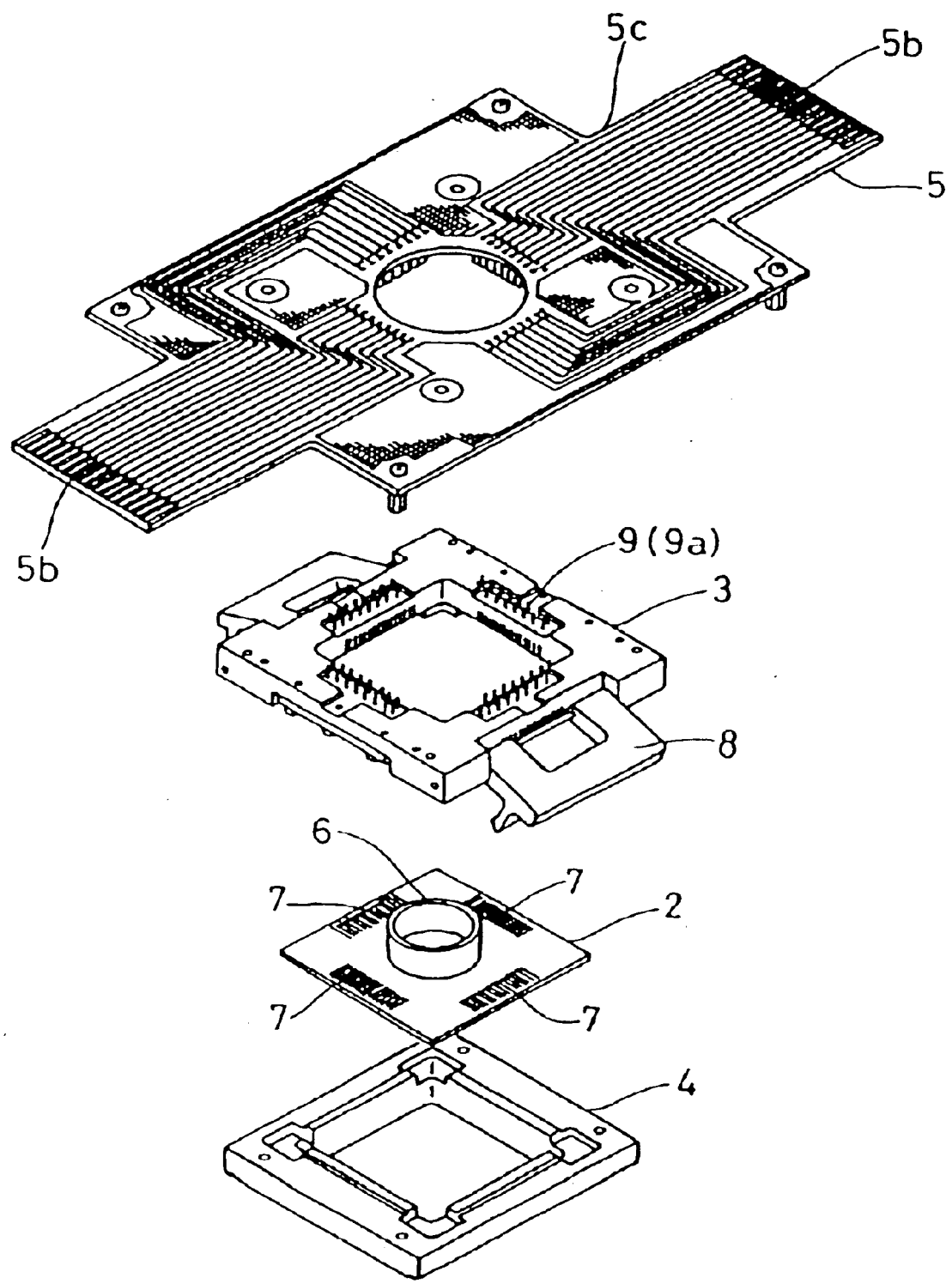
F I G. 2

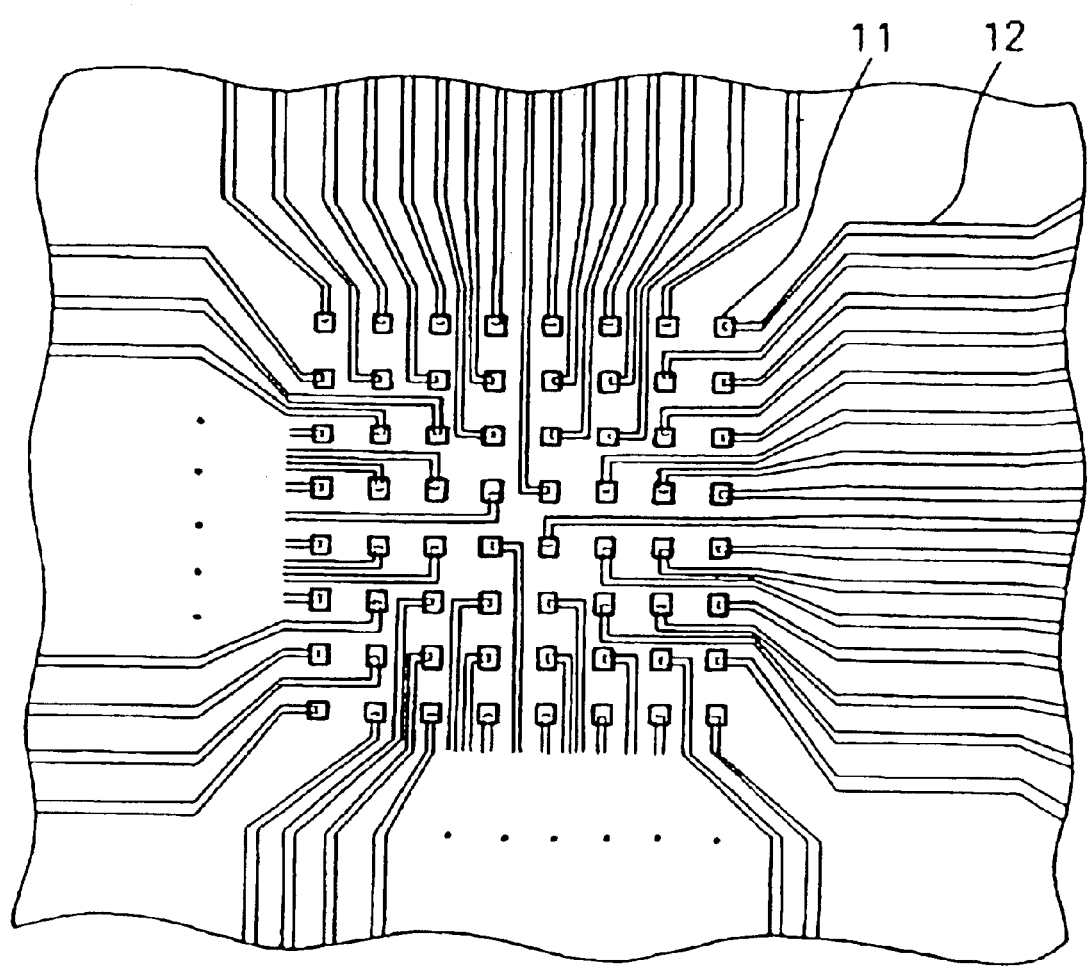
F I G. 3
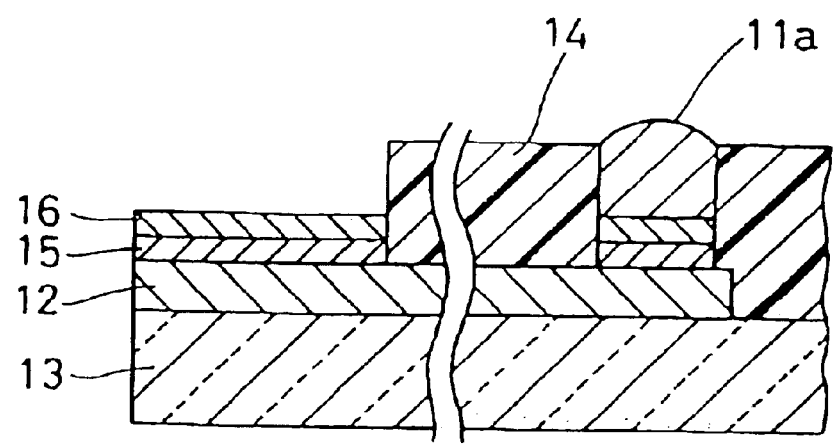
F I G. 4

F I G. 1 0 (a) 
F I G. 1 0 (b) 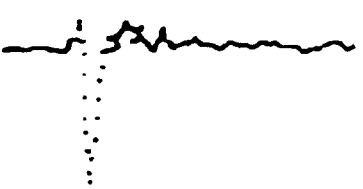
F I G. 1 0 (c) 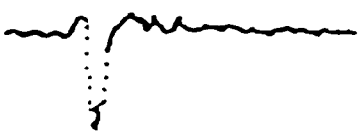
F I G. 1 0 (d) 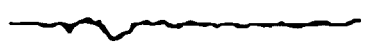
F I G. 1 0 (e) 

0.2mv
15msec

F I G. 1 2 (a)
F I G. 1 2 (b)

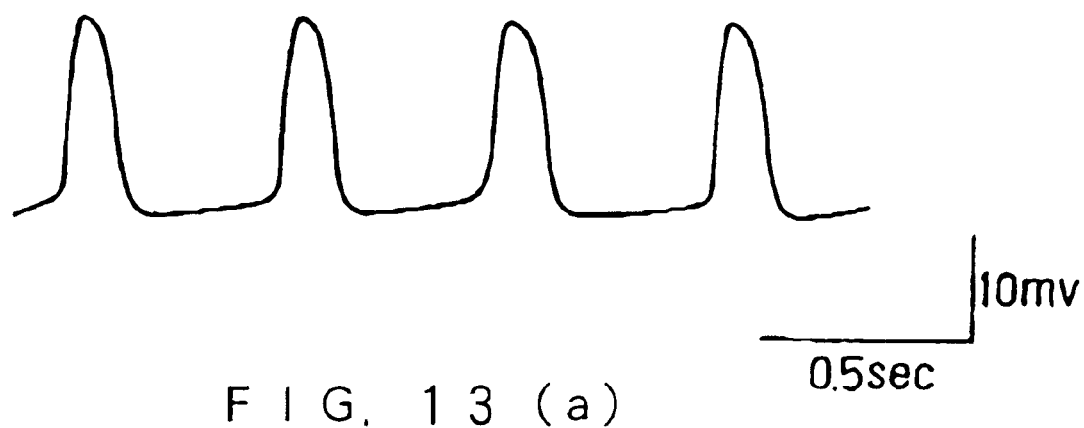
F I G. 1 3 (a)
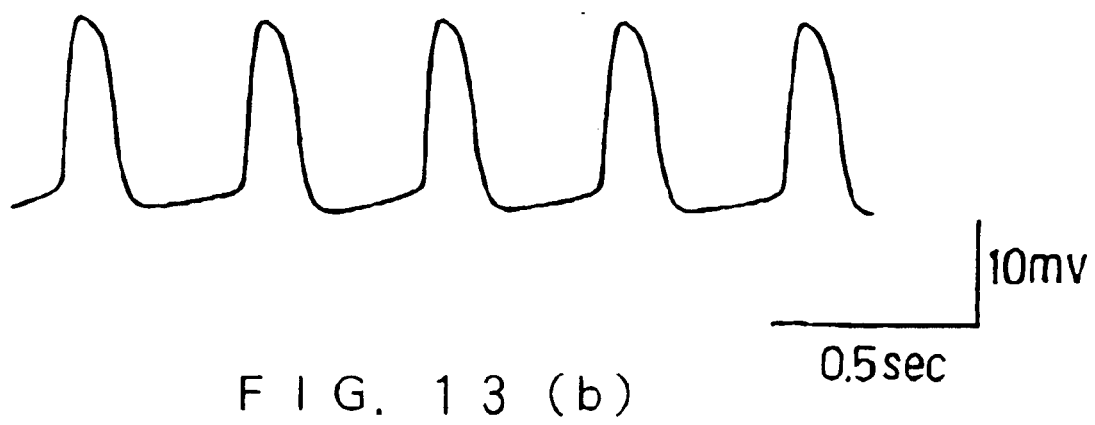
F I G. 1 3 (b)

METHOD FOR MEASURING PHYSIOCOCHEMICAL PROPERTIES OF TISSUES OF CELLS, METHOD FOR EXAMINING CHEMICALS, AND APPARATUS THEREFOR

FIELD OF THE INVENTION

This invention relates to measuring the physical and chemical properties of biological tissue or cells depending on a change in the physical and chemical environment, a method and a device for examining the effect of a variety of medicines administered to the tissue or cells, such as medicines for the central nervous system, and is mainly of application in the fields of environmental science, medicine, pharmacology, nutritional science and neurobiology.

BACKGROUND OF THE INVENTION

In recent years, with the installation of power lines and the use of electrical appliances such as mobile phones, computer monitors and the like, the presence of strong electromagnetic fields has become a familiar phenomenon. Moreover, with the progress in pharmacology, nutritional science and organic chemistry, new medicines and food additives as well as chemical substances hitherto unknown to nature are constantly under development. To elucidate the influence that these artificial physical and chemical environmental factors have on biological matter, investigations with statistical techniques focusing on humans and experiments with animals have been performed.

However, in investigations with statistical techniques focusing on humans, it is extremely difficult to provide constant conditions for a population, and a rather long investigation time is necessary. Furthermore, in humans there are subtle differences with respect to their individual genetic background, their way of life, their past eating habits and so on. For example, let us suppose, that we select high voltage power lines as a source of electromagnetic waves near our bodies to examine the capacity of electromagnetic waves to cause cancer in a human body. In that case, it is very difficult to account for different examination conditions among those living near the high voltage power line concerning their genetic history, nutritional history, classification of cancer ridden organs, age, body weight, sex, personal preferences, medical history and virus infections. When the statistical examinations are performed, it is necessary to perform enough model experiments using laboratory animals for which the above conditions can be adjusted easily. Then, it is important to perform experiments at the tissue level, especially with networks of cells, which is not possible with the experiments described above. In the field of pharmacology, for example on the way towards the development of a new medicine for the central nervous system, rather than using the brain of a laboratory animal, an isolate nervous cell is prepared, dispersed and cultivated, and the effect of the new medicine is examined on the individual cell level under pharmacological, electrophysiological, morphological and immunological aspects. However, the cerebral nervous functions are controlled by a nervous circuitry of systematically accumulated nervous cells. Therefore, if the brain's high order functions are taken to be governed by the general behavior of the nervous circuitry, then there can be no doubt that it is very important to elucidate the influence of those medicines on the nervous circuitry, as has already been stated above. Nevertheless, the reason why the influence of medicines on the nervous circuitry and on the intracellular network at the organic level has not been examined in the past is that first of all, there was no technique of screening the nervous circuitry with brain slices. Therefore, in the present situation, various kinds of medicines are tested with the usual pharmacological experiments and come to practical use, while their operational mechanism in the nervous circuitry is still unclear. For example, the famous insomnia medicine Halcion is thought to suppress excessive nervous activity of the limbic and the cerebral cortex due to a functional exasperation of GABA receptors accompanying the excessive polarization of nervous cells. However, this effect became clear by using individual nervous cells, yet it is by no means clear, what influence is exerted on the entire nervous circuitry. The schizophrenia medicines haloperidol and chlozapine are likewise administered without examining their influence on the nervous circuitry. On the other hand, medicines that show an enormous effect on the nervous circuitry and have few side effects may often not be deemed to be effective when subjected to conventional screening methods, and there is a possibility that they do not come to practical use.

The necessity of research on the biological organ level is being recognized not only for the functional explanation of the nervous circuitry but also for research on other biological organs, and in biological fields such as medicine and pharmacology there is an earnest desire for the development of a device which realizes this research efficiently and with high reliability.

Thus, the development of a device that can be used to observe with time the physical and chemical properties of tissue or cells extracted from biological matter, and maintain the physical and chemical environment near the tissue or cells constant, yet enables controlled change of the physical and chemical environment near the tissue or cells for experimental purposes, and the simultaneous investigation of a large amount of samples is strongly desired.

The purpose of the present invention is to provide a method of testing medicines and a device for the same, and a method of measuring the physical and chemical properties of tissue or cells and a device for the same, and thus to match the above desires.

SUMMARY OF THE INVENTION

In order to attain the above purposes, the method of measuring the physical and chemical properties of biological tissue or cells of the present invention is a method for the observation of the influence, that a change of the physical and chemical environment surrounding the biological tissue or cells has on the physical and chemical properties of the biological tissue or cells, wherein the physical and chemical environment surrounding the biological tissue or cells is held constant, then the physical and chemical environment is arbitrarily changed, the physical and chemical properties of the tissue or cells are observed, and the physical and chemical properties of the tissue or cells before and after the change of the physical and chemical environment are compared.

As has been described above, in the measurement of the physical and chemical properties of biological tissue or cells of the present invention, the physical and chemical properties are observed while the physical and chemical environment is preserved in a constant condition, then a part or all of the physical and chemical environment is changed, and the physical and chemical properties of the tissue or cells are observed again. Thus, the influence that the change of the physical and chemical environment has on the tissue or cells can be made clear by comparing the physical and chemical properties of the tissue or cells before and after changing the physical and chemical environment. If for example, the physical and chemical environment is changed by adding chemical substances, then the influence of the added chemical substance on the biological matter can be examined with this measurement method. Or, if for example the physical and chemical environment is changed by applying a magnetic field, then the influence of the applied magnetic field on the biological matter can be examined with this measurement method.

The preferred embodiment of this method of measuring physical and chemical properties of tissue and the like observes the physical and chemical properties of biological tissue or cells using a device comprising at least a cell culture system, an environmental adjustment system, an observation system and a comparison system, and comprises the following processes (A)–(E):

(A) a process step of culturing the tissue or cells with the cell culture system, or maintaining a first physical and chemical environment near the tissue or cells with the cell culture system, (B) a process step of observing the first physical and chemical properties of the tissue or cells in the first physical and chemical environment with the observation system, (C) a process step of changing the first physical and chemical environment into a second physical and chemical environment with the environmental adjustment system, (D) a process step of observing the second physical and chemical properties of the tissue or cells in the second physical and chemical environment with the observation system, and (E) a process step of comparing the first physical and chemical properties of the tissue or cells to the second physical and chemical properties of the tissue or cells with the comparison system.

In the method according to this preferred embodiment, the physical and chemical properties of the tissue or cells can be measured easily.

Moreover, in an especially preferred embodiment the process of changing the first physical and chemical environment into a second physical and chemical environment comprises the replacement of a first culture medium used in the cell culture system with a second culture medium used in the cell culture medium. In that case, it is preferable that the first and the second culture medium comprise one or more medicines of arbitrary concentration.

The measurement device for physical and chemical properties of biological tissue or cells of the present invention is a device for observing the influence that a change of the physical and chemical environment surrounding the biological tissue or cells has on the physical and chemical properties of the tissue or cells, and comprises the following systems (A)–(E):

(A) a cell culture system for culturing the tissue or cells, or maintaining a physical and chemical environment near the tissue or cells, (B) an observation system for observing the physical and chemical properties of the tissue or cells in a first physical and chemical environment, (C) an environmental adjustment system for adjusting the physical and chemical environment maintaining the tissue or cells, (D) an observation system for observing the physical and chemical properties of the tissue or cells after the first physical and chemical environment has been changed into a second physical and chemical environment with the environmental adjustment system, and (E) a comparison system for comparing the physical and chemical properties in the first physical and chemical environment to the physical and chemical properties in the second physical and chemical environment.

In this device, it is preferable that the environmental adjustment system comprises a system for adding chemical substances, microorganisms or viruses to the culture medium used by the cell culture system, and a system for replacing a first culture medium comprising one or more chemical substances, microorganisms or viruses of arbitrary concentration in the cell culture system with a second culture medium comprising one or more chemical substances, microorganisms or viruses of arbitrary concentration.

The chemical substances are not limited to artificially produced chemical substances, but a rather broad concept is intended, also including natural chemical substances such as proteins, nucleic acids, saccharides, and lipids.

Furthermore, in this device, it is preferable that the environmental adjustment system comprises a system for adding substances to a culture medium used by the cell culture system, and a system for replacing a first culture medium used by the cell culture system with a second culture medium used by the cell culture system.

Furthermore, it is preferable that the observation system is an electric potential measurement device for the measurement of the electrophysiological properties of the tissue or cells, and comprises the following (A) and (B):

(A) an integrated cell placement device comprising (a) a plurality of microelectrodes on a substrate, (b) a cell placement portion for placing the tissue or cells on the microelectrodes, and (c) an electrical connector for applying an electric signal to the microelectrodes and deriving an electric signal from the microelectrodes, and (B) a processing system for processing the output signal produced by the electrophysiological activity of the tissue or cells connected with an electrical connector of the integrated cell placement device.

Furthermore, it is preferable that the observation system further includes in addition to (A) and (B):

(C) a system for applying an electric stimulus to the tissue or cells connected with an electrical connector of the integrated cell placement device.

According to this preferred type of device, for example the observations described below become possible.

A sample of tissue or cells is set in the cell placement portion of the integrated cell placement device, and more than one microelectrode is connected to the tissue or cells. A stimulus signal can be applied between an arbitrary pair of electrodes via the electrical connector by the system for applying an electric stimulus. The transient change of the potential induced in the other electrodes is transmitted via the electrical connector to the signal processing system, and after the necessary signal processing is finished, the signal can for example be given out to a display device and be stored in a memory device. Next, the physical and chemical environment is changed and the same measurement is repeated. Then the measurement results before the change of the physical and chemical environment, which are stored in the memory device, are recalled and compared to the measurement results after the change of the physical and chemical environment. Moreover, a similar measurement of the spontaneous potential without the application of a stimulus signal is performed.

In this preferred embodiment of the present invention, because the measurement is performed with a systematic series of processes, the measurement of the physical and chemical properties of tissue and the like can be performed with high efficiency, and is advantageous for large scale measurements as are necessary for example for the screening of medicines. Furthermore, with the preferred embodiment of the device of the present invention the activity potential of biological organs (for example a brain or heart slice of a mouse) can be easily measured. Hitherto, decisions were often based on pharmacological tests such as shrinkage tests on the cell level or in entire biological organs, but the device of the present invention makes it possible to perform interregional interaction tests with many points. As a result, it is possible to detect even effects that are cancelled out when regarded in their entirety, and to obtain data with high reliability. This is also advantageous with respect to performing screening tests and the like efficiently but with rather low costs.

Furthermore, with this preferred embodiment of the present invention, the physical and chemical properties of a plurality of tissue or cell samples can be measured while culturing those samples with a plurality of integrated cell placement devices. Thus, the device comprising a multi-array of integrated cell placement devices can make the measurements much more efficient, because it is possible to process a plurality of tissue or cell samples simultaneously, and is thus most suitable as a screening device for medicines necessitating large scale sample processing.

It is preferable that in the above device, the plurality of integrated cell placement devices further comprises an environmental adjustment system for individual adjustment of the physical and chemical environment of the tissue or cell samples.

Next, the method of testing medicines of the present invention comprises: providing a detector for detecting the electrical properties of the tissue or cells to which chemical substances, microorganisms or viruses have been added; providing an image detection system for observing the visible properties of the tissue or cells from outside; measuring the electrical or visible properties of the tissue or cells when chemical substances, microorganisms or viruses have been added to the tissue or cells; and judging from those two properties whether the added chemical substances, microorganisms or viruses have had an influence on the tissue or cells.

Furthermore, the medicine testing device of the present invention is provided with an electrical measurement portion for the measurement of the electrical properties of tissue or cells to which chemical substances, microorganisms or viruses have been added, and a visible properties detection portion for the measurement of visible properties of the tissue or cells, and the influence that the chemical substances, microorganisms or viruses have on the tissue or cells can be measured from the output of the electrical measurement portion and the visible properties detection portion.

BRIEF DESCRIPTION OF THE DRAWINGS

FIG. 2 is an assembly drawing of the integrated cell placement device.

FIG. 3 shows a planar view of 64 microelectrodes employed in the center of an integrated multiple electrode forming the integrated cell placement device, and the wiring pattern of those 64 microelectrodes.

FIG. 4 shows a diagrammatic cross-section of an integrated multiple electrode.

FIGS. 10(a)–(e) show the acute effect that methamphetamine has on the induced potential of the cultivated cells, measured with a device according to the present invention.

FIGS. 12(a) and (b) show the chronic effect that acetylcholine has on the spontaneous activity potential of the cultivated cells, measured with a device according to the present invention.

FIGS. 13(a) and (b) show the chronic effect that adrenaline has on the spontaneous activity potential of the cultivated cells, measured with a device according to the present invention.

DETAILED DESCRIPTION OF THE INVENTION

The preferred embodiments of the present invention are explained below with reference to the drawings.

Figure 1:
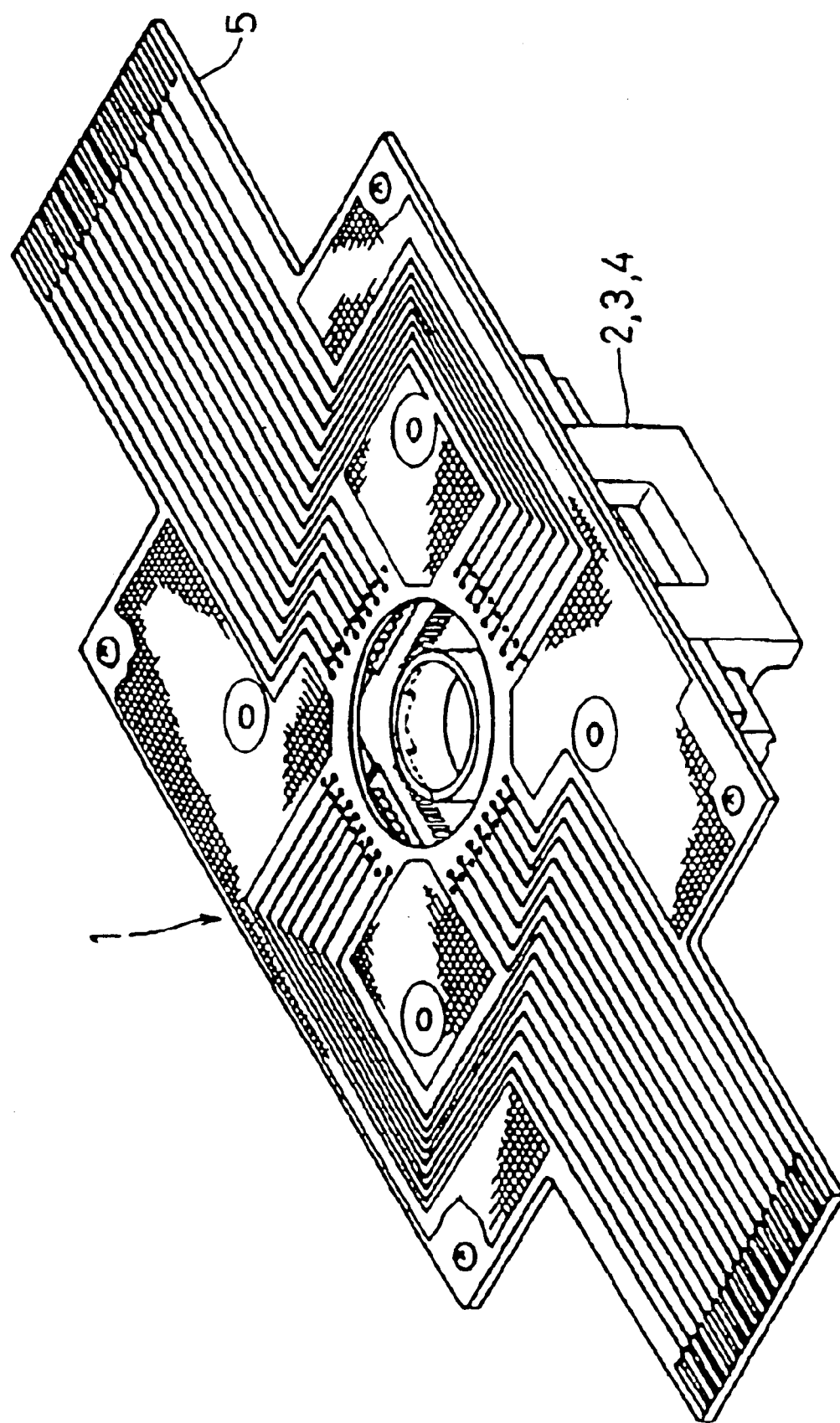
FIG. 1 shows a perspective view of an integrated cell placement device used in a cell potential measurement device according to a preferred embodiment of the present invention.

First of all, the integrated cell placement device used in the measurement device of the present invention is explained. As is shown in a perspective view in FIG. 1 and an assembly drawing in FIG. 2, this integrated cell placement device includes an integrated multiple electrode 2 comprising microelectrodes and their wiring pattern on a glass plate, two brace holders 3, 4 which sandwich and vertically fasten the integrated multiple electrode 2, and a printed circuit board 5 fastening the holders.

The integrated multiple electrode is almost the same as disclosed in the Publication of Unexamined Patent Applications No. Hei 6-78889. In the center of a substrate made from a 1.1 mm thick and 50 mm square transparent pyrex glass, a matrix of 64 microelectrodes 11 is formed and every microelectrode is connected via a wiring pattern 12 (see FIG. 3). Every electrode 11 is a 50 µm square (with an area of $25 \times 10^2$ µm$^2$), and the distance between the centers of neighboring electrodes is 150 μm. In four regions of the substrate, 16 electric contact points each (thus 64 in total) are formed (see FIG. 2). These electric contact points 7 are connected to their corresponding microelectrodes in the center of the substrate with the wiring pattern 12. The 16 contact points in each region are lined up with a 1.27 mm pitch. The manufacturing method for the integrated multiple electrode 2 is explained below with reference to the sectional drawing of FIG. 4. For illustrative reasons, the scales of FIG. 4 are not proportional.

A 150 nm thick ITO (indium tin oxide) film is applied to the surface of the glass plate 13, and the wiring pattern 12 is formed with photo resist and etching. On top of that, a 1.4 μm thick polyimide film and an insulating film 14 are applied. The ITO film is exposed at the location of the microelectrodes and the electric contact points, where a 500 nm thick nickel-plating 15 and a 50 nm thick gold-plating 16 are employed. A cylindrical polystyrene frame or a cylindrical glass frame 6 (see FIG. 2) with an internal diameter of 22 mm, an external diameter of 25 mm and a height of 10 mm is glued to the surface of the insulating film 14 on the glass plate 13 with a silicone type adhesive. This cylindrical polystyrene or glass frame 6 is fixed after aligning it with the center of the glass plate 13, that is the center of the 64 microelectrodes 11. The inside of this polystyrene or glass frame 6 corresponds to a cell placement portion. Platinum black 11a is deposited on the surface of the gold-plating of the microelectrode 11 by filling it with a solution of 1% by mass chloroplatinic acid, 0.01% by mass lead acetate and 0.0025% by mass hydrochloric acid, and letting a current of 20 mA/cm$^2$ flow for one minute.

Figure 5A:
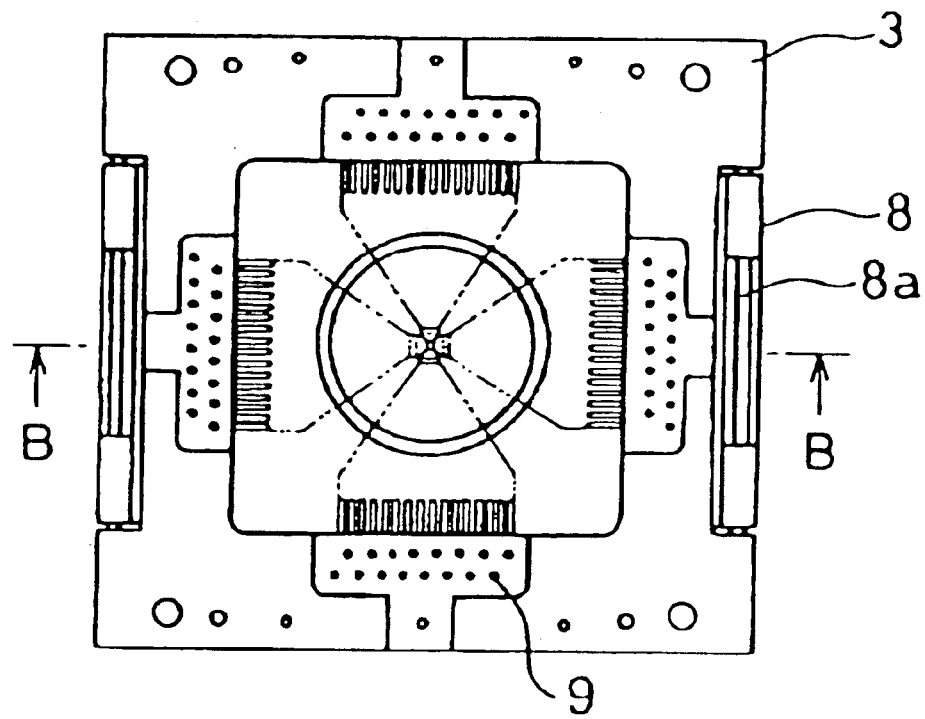
FIGS. 5(A) and (B) show a planar view of the top of the integrated multiple electrode and a sectional view of the integrated multiple electrode when the bottom holders are in a fastening position.

Next, the two brace holders 3 and 4, which vertically sandwich the integrated multiple electrode 2, are explained. The holders 3 and 4 are formed with a resin, and are provided with a rectangular opening and step-shaped portions for holding the edge portions of the integrated multiple electrode 2, as is shown in FIG. 2. The upper holder 3 is provided with a pair of fasteners 8 and 16×4 contact metal fittings 9. FIG. 5(A) shows a top view, FIG. 5(B) a sectional view along the plane B—B, and FIG. 6 a perspective flip side view of the holders 3 and 4 sandwiching and fastening the integrated multiple electrode 2. As can be understood from these drawings, the fasteners 8 are pivoted with the pivot pin 8 at two opposite edges of the holder 3. Furthermore, grooves 4a are formed in two opposite edges of the rear surface of the lower holder 4, and convex braces 8b are engaged in the grooves 4a, so that the vertical holders 3 and 4 tightly fasten the integrated multiple electrode 2 in a sandwiching manner.

Figure 7:
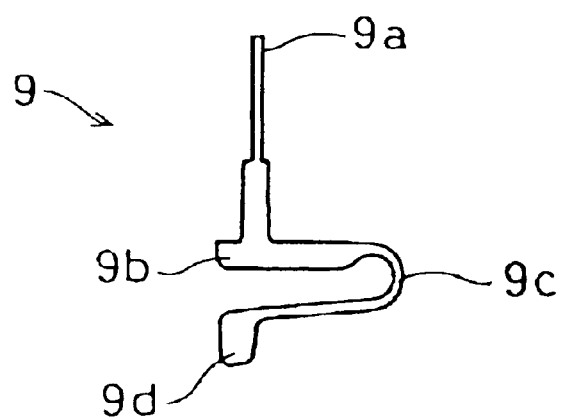
FIG. 7 is a side view of the metal contact fittings for the vertical holder.

The 64 contact metal fittings 9, which are employed in the upper holder 3 and correspond to the electric contact points 7 of the integrated multiple electrode 2, are formed into the shape shown in FIG. 7 by processing a metal plate with high flexibility and conductivity, such as is obtained by applying a nickel- and gold-plating to BeCu. The contact metal fittings 9 include a pin 9a, a base portion 9b, a bent portion 9c, and a movable contact portion 9d extending from the base portion 9b via the bent portion 9c. This configuration makes an elastic displacement of the movable contact portion 9d relative to the base portion 9b possible. 64(16×4) through holes for inserting the pin 9a of the contact metal fittings 9 and 64 (16×4) grooves for engaging the base portion 9b are formed in the upper holder 3.

Figure 5B:
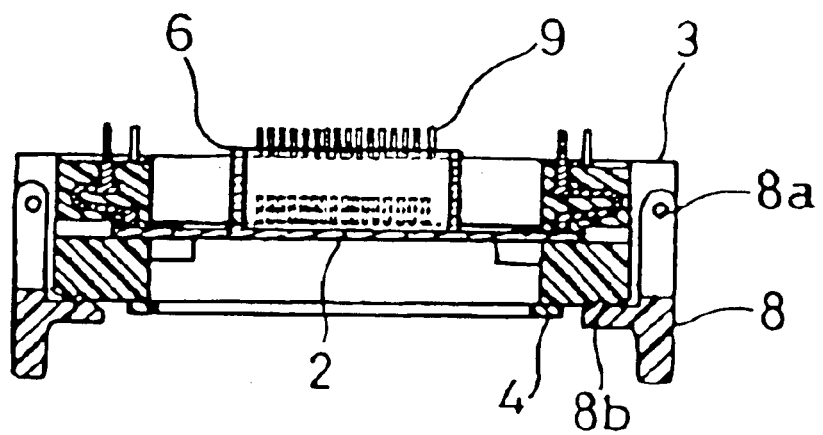
Figure 6:
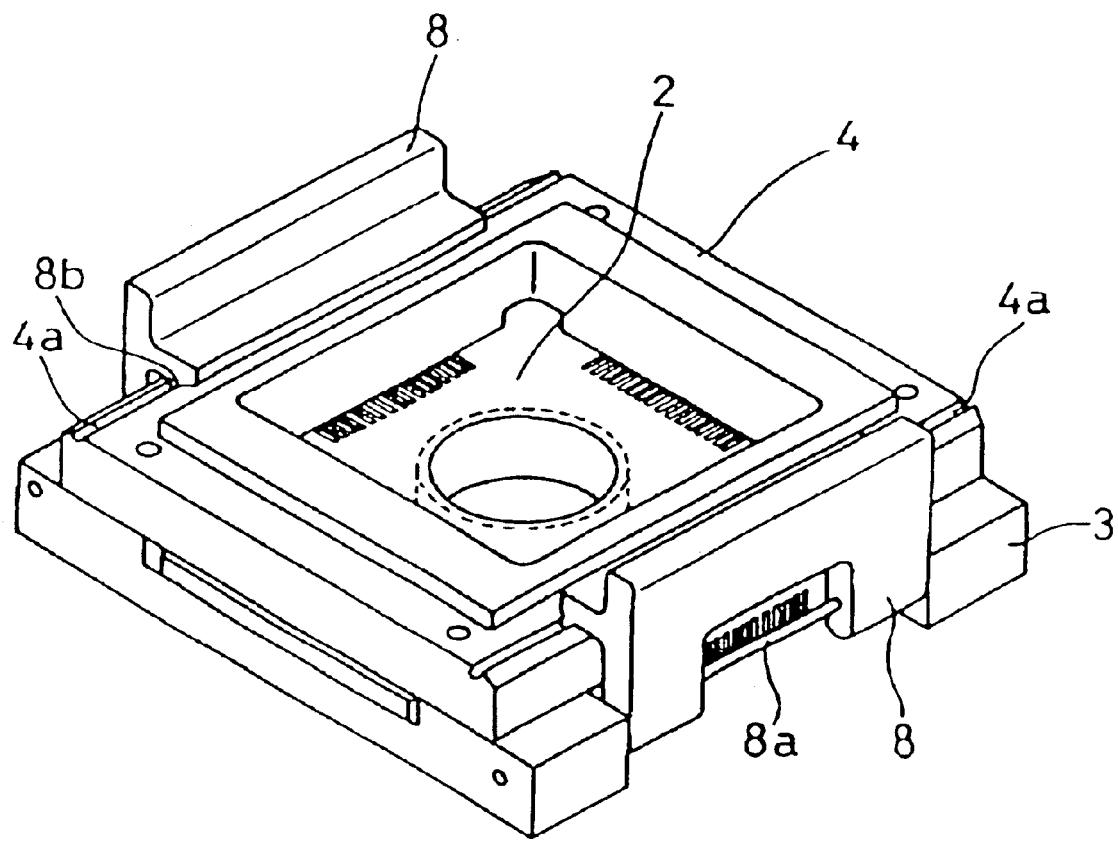
FIG. 6 is a perspective view of the integrated multiple electrode and the vertical holder of FIG. 5.

As is shown in FIGS. 2 and 5(B), the contact metal fittings 9 are fastened by inserting them in the above mentioned through holes and grooves, and the pins 9a protrude from the upper holder 3. Two kinds of contact metal fittings 9 with differing lengths of the base portion 9b are employed together and the 16 pins 9a protruding from the upper holder 3 are arranged in two staggered rows. As will be pointed out below, these pins 9a are connected to connectors for external connection installed on the printed circuit board 5.

The movable contact portion 9d of the contact metal fitting 9 protrudes from the rear side of the upper holder 3, when the contact metal fitting 9 is inserted in the through hole and grooves of the upper holder 3 and fastened. This state is illustrated in the assembly drawing of FIG. 8, which is a flip side view of drawing 2. In the state of sandwiching and fastening the integrated multiple electrode 2 with the holders 3 and 4, the movable contact portions 9d of the contact metal fittings 9 touches the electric contact points 7 of the integrated multiple electrode 2, and a certain contact pressure is exerted on the contact portions through flexible deformation of the bent portions 9c. Thus, the electric contact points 7, which are connected via the wiring pattern 12 to the microelectrodes of the integrated multiple electrode 2, are electrically connected to the contact metal fittings 9 with a small contact resistance (below 30 mΩ).

Next, the printed circuit board 5 is explained. The printed circuit board 5 fastens together the structure obtained by assembling the integrated multiple electrode 2 and the holders 3 and 4, and fulfills the function of providing an electrical connection between the microelectrodes 11 of the integrated multiple electrode 2 and the connectors to the outside via the wiring pattern 12, the electric contact points 7 and the contact metal fittings 9. Furthermore, the printed circuit board 5 is intended to facilitate handling such as installation in the measurement device.

Figure 8:
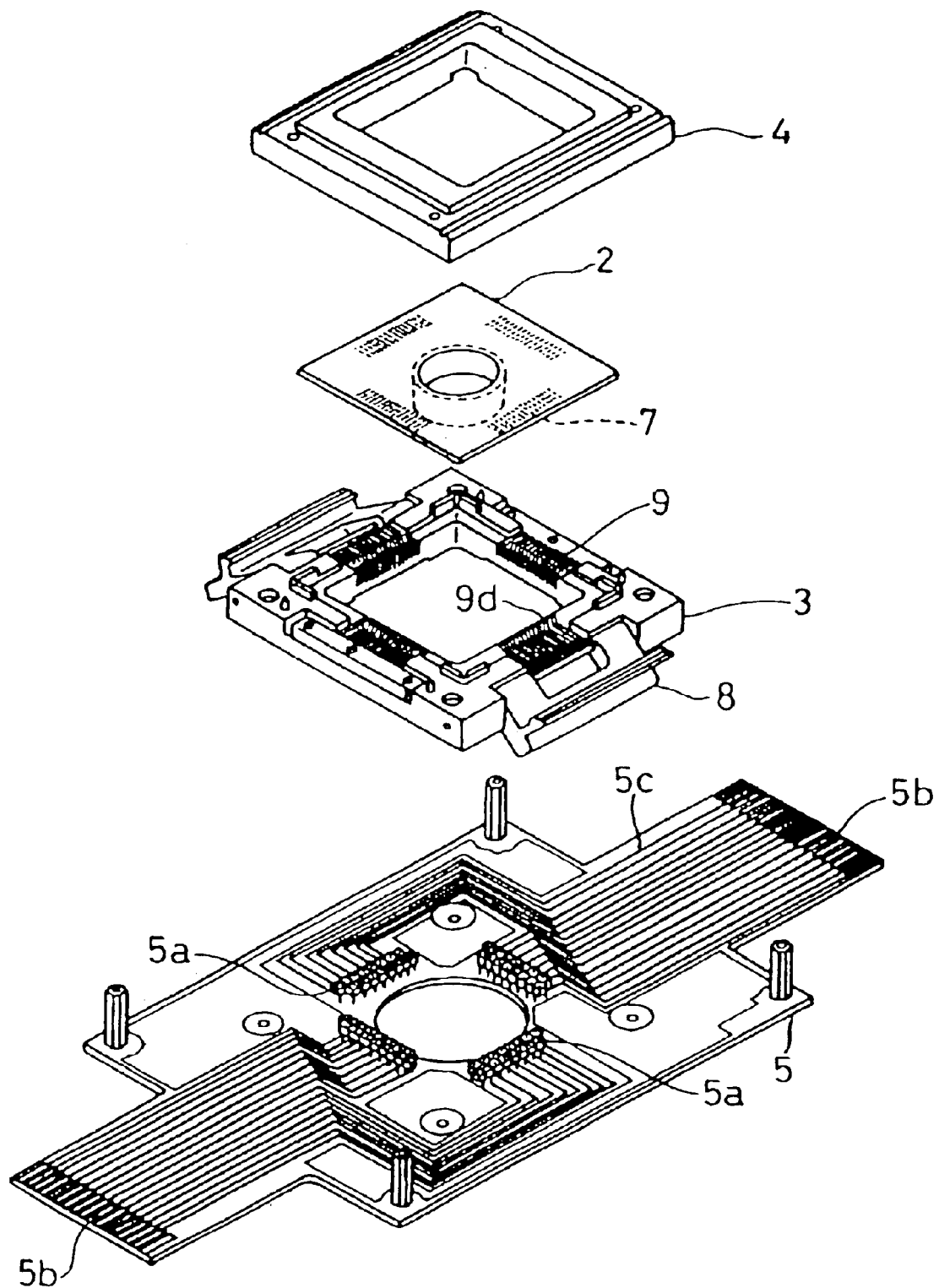
FIG. 8 is an assembly drawing of the integrated cell placement device seen from a viewpoint opposite of the one in FIG. 2.

The printed circuit board 5 is formed from a glass epoxy substrate, which is patterned on both sides, and connectors 5a are provided at four places in the center of the rear side shown in FIG. 8, near the circular opening. By inserting the 16 pins 9a, protruding in two staggered rows from the surface of the upper holder 3 in four places, into the corresponding connectors 5a, the structure obtained by assembling the integrated multiple electrode 2 and the holders 3 and 4 is fastened and electrically connected to the printed circuit board 5.

Electric contact points are formed with 2.54 mm pitch for double sided edge connectors on edge portions 5b on both sides of the printed circuit board 5, and those electric contact points are connected to the connectors 5a in the center with the wiring pattern 5c. The inner row of connectors 5a is wired on the front surface, the outer row is wired on the rear surface. 32 electric contact points are formed on each of the two edge portions 5b, which adds up to 64 electric contact points In order to secure the mechanical stability of the arrangement, the upper holder 3 can be fastened to the printed circuit board with screws.

Figure 9:
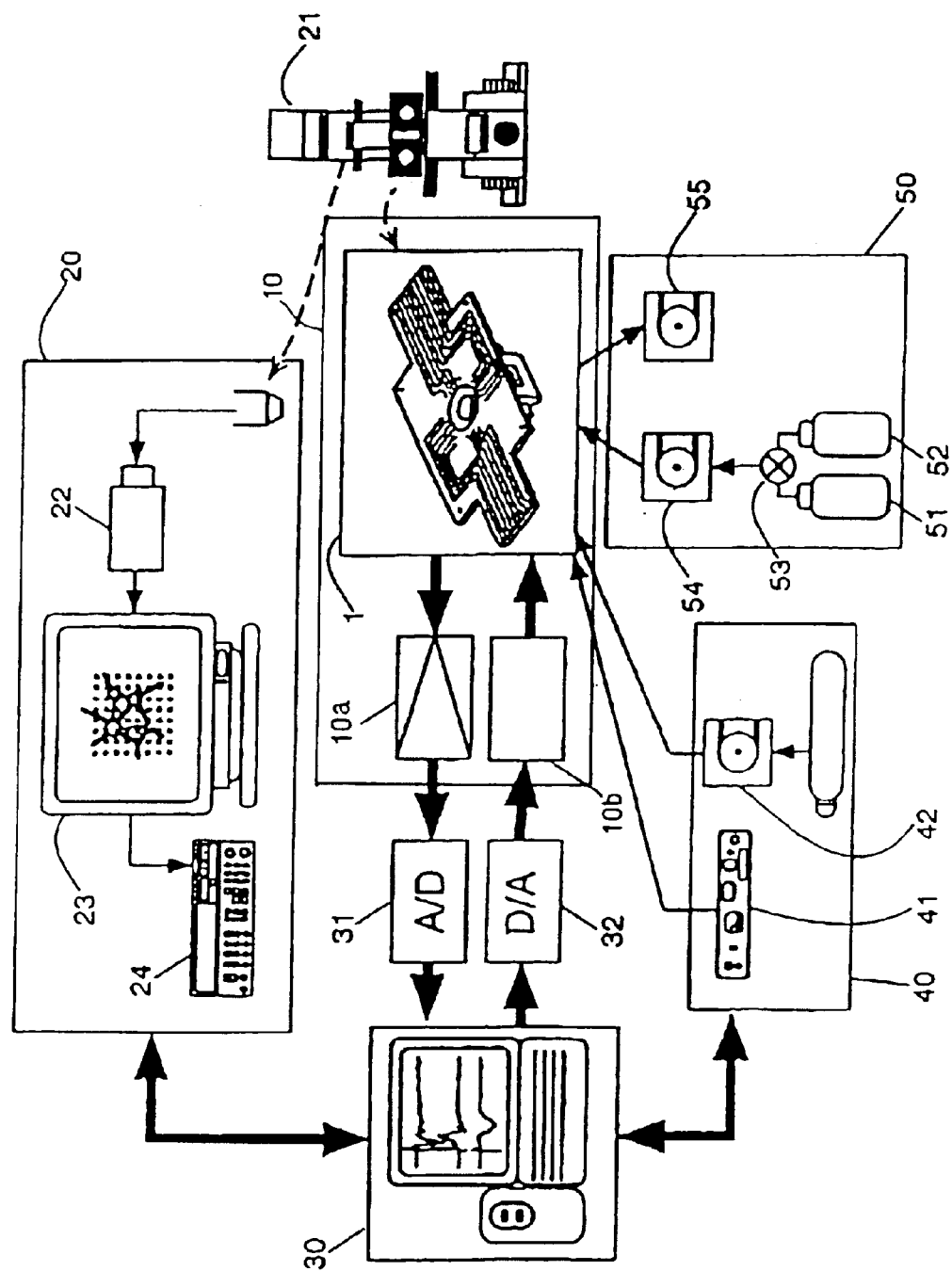
FIG. 9 is a block diagram of a device according to the present invention.

FIG. 9 shows a favorable embodiment of a cell potential measurement device using an integrated cell placement device 1 configured as explained above. The measurement device according to this embodiment comprises: the previously mentioned integrated cell placement device 1; an image detection system 20 comprising an inverted microscope 21 for optically observing the cells placed on the integrated cell placement device 1; a detector 10 for detecting the electrical properties of the cells; a system for applying a stimulus signal to the cells; a computer 30 comprising a system for processing and comparing the output signal from the cells; a cell culture system 40 for maintaining a culture atmosphere for the cells; and an environmental adjustment system 50 for adding arbitrary chemical substances in arbitrary concentrations to a culture fluid, or removing the added chemical substances.

In addition to the inverted microscope 21 (Olympus IMT-2-F or IX70 or equivalent) on which the integrated cell placement device is place, the image detection system 20 comprises an SIT camera 22 (Hamamatsu Photonics C2400-08 or equivalent), a high precision display 23, and an image file device 24 (Matsushita El. Ind. TQ-2600 or FTQ-3100F or equivalent). However, it is possible that the display of the computer 30 also serves as the high precision display 23. Moreover, the equipment mentioned in brackets is only an example of the equipment that can be employed. As in all such cases in the following, this is by no means to be understood as a limitation.

As for the computer 30, a Windows compatible personal computer equipped with an A/D conversion board and measurement software is suitable. The A/D conversion board comprises an A/D converter 31 and a D/A converter 32, as shown in FIG. 9. The A/D converter 31 has 12 bits, 64 channels, whereas the D/A converter 32 has 12 bits, 8 channels.

The measurement software comprises software to set the conditions for the application of a stimulus signal and the conditions for the recording of the obtained detection signal. With this measurement software, the computer 30 controls not only the system for applying a stimulus signal to the cells and the system for processing and comparing the output signal from the cells, but also the image detection system 20 (SIT camera and image file device) and the cell culture system 40. Below, the main structure of the measurement software is explained screen by screen.

With a parameter setting screen, it is possible to devise complicated stimulus conditions by drawing a stimulus waveform on the screen using a keyboard or a mouse. Moreover, the settings of the recording conditions with 64 input channels and 10 kHz sampling rate can handle several hours of consecutive recording. Furthermore, which electrodes apply a stimulus signal and which electrodes pick up a detection signal can be designated by indicating them with a mouse or a pen on the microscope image displayed on the screen. Furthermore, the adjustment of conditions such as the temperature or the pH-value in the cell culture system 40, the switching of valves or pumps, or the pump flow velocity in the environmental adjustment system 50 can be performed using the keyboard.

With a recording screen, the cell's detected spontaneous activity potential or induced potential can be displayed in real-time for all 64 channels.

When a stimulus signal is given out from a computer 30 as described above, then this stimulus signal is passed through the D/A converter 32 and an isolator 10 b (BAK ELECTRONICS BSI-2 or equivalent) comprised in the system 10 for detecting electrical properties, and applied to the cells. The stimulus signal can be applied between two points selected from among the 64 microelectrodes 11 of the integrated cell placement device. Then, the induced potential occurring between each of the microelectrodes 11 and ground level (potential of the culture fluid) is passed through a 64 channel high sensitivity amplifier 10a (Nihon Kohden AB-610J or equivalent) and the A/D converter 31, and is entered into the computer 30.

Next, the cell culture system 40 comprises a temperature adjustment device 41, and a means 42 for supplying a mixed gas of air and carbon dioxide. The cell culture system 40 is formed by a microincubator PDM I-2 manufactured by Medical Systems or an equivalent product, a temperature controller TC-202 or an equivalent product, and a $CO_2$ tank or the like. The temperature of the microincubator can be controlled in the range of 0–50° C. with a Peltier element, the rate of fluid flow can be regulated up to 3.0 mL/min, and the rate of gas flow can be regulated up to 1.0 mL/min. It is also suitable to use a microincubator with an internal temperature controller (Olympus IMT2—IBSV or equivalent).

Then, the environmental adjustment system comprises a fluid bottle 51, a fluid bottle 52, a valve 53, a pump 54 and a pump 55. The fluid bottle 51 contains a regular culture fluid, whereas the fluid bottle 52 contains the regular culture fluid in which arbitrary chemical substances are dissolved in arbitrary concentrations, in other words, the fluid bottle 52 contains the fluid with the substances to be tested. It is possible to decide by operating the valve 53 whether the culture fluid or the testing fluid is to be supplied to the integrated cell placement device 1 with the pump 54. Then, the pump 55, which is set to the same flow velocity as the pump 54 and operates simultaneously, sucks in the fluid from the integrated cell placement device 1. In this manner, the fluid composition inside the integrated cell placement device 1 can be altered while holding the fluid amount constant.

The device described above is an example provided with one integrated cell placement device, however the present invention is by no means limited to that number. It is also possible to form more than one integrated multiple electrode on a glass plate, and to form more than one polystyrene frame or glass frame on those electrodes. A device comprising such a multi-array of integrated cell placement devices can make the measurements much more efficient, because it is possible to process a plurality of tissue or cell samples at the same time, and is thus most suitable as a screening device for medicines necessitating large scale sample processing.

Figure 14:
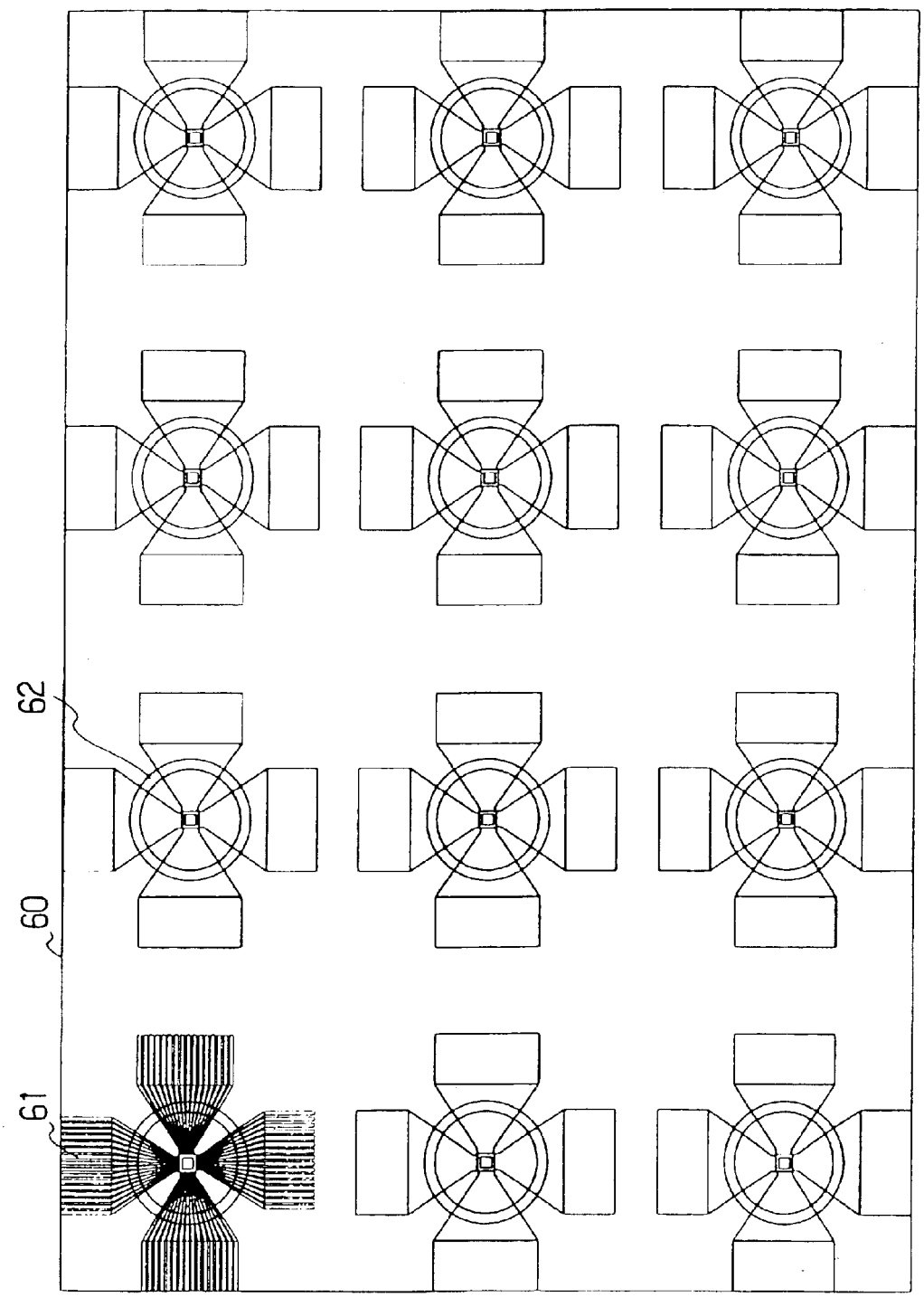
FIG. 14 is a top view showing an example of the multiple formation of integrated multiple electrodes in a multi-array.

FIG. 14 illustrates a multi-array example of 3×4 (thus 12 in total) integrated multiple electrodes. As is shown in this drawing, the microelectrodes 11 and their wiring pattern 12 (see FIG. 3) are laid out 3 by 4 (thus 12 in total), and form a multi-array of integrated multiple electrodes 60 (called multi-array below). The center portion of their wiring pattern is equal to the wiring pattern of the integrated multiple electrode 2 shown in FIG. 3, 64 microelectrodes 11 are formed in an 8×8 matrix, and each microelectrode is connected with the wiring pattern 12. The electrode size (50 $\mu$m square) and the distance between the centers of neighboring electrodes is the same as in the integrated multiple electrode 2. Moreover, in the same drawing, the microelectrodes 11, the wiring pattern 12 and the electric contact points 61 are concretely illustrated in one instance only, all other cases are drawn in abbreviated form.

In four regions of each pattern, 16 electric contact points 61 each (thus 64 in total) are formed, and these electric contact points 61 are connected to their corresponding microelectrodes 11 in the center of the pattern via the wiring pattern 12. Different from the integrated multiple electrode 2, the 16 electric contact points 61 in each of the regions are aligned with a 0.635 mm pitch, in order to achieve an overall size of the multi-array that is easy to handle (84 mm long, 127 mm wide).

As is shown in the drawing, by laying out the same pattern in a 3×4 matrix in this multi-array 60, the length of all the wiring patterns is almost constant. Therefore, the resistance of the wiring pattern 12 is almost constant, and it is possible to obtain multi-arrays 60 that are suitable for electrical and physiological measurements. If for example the microelectrodes 11 are arranged in the same position as in FIG. 14, all the electric contact points 61 are arranged on the edge of a pyrex glass substrate, and the wiring pattern 12 is laid out so that each microelectrode 11 is connected to one electric contact point 61, then a considerable difference between the length of the wiring pattern 12 from the microelectrodes located in the peripheral regions of the substrate and the length of the wiring pattern 12 from the microelectrodes located in the central region of the substrate arises. Therefore, a considerable difference in the resistance of the wiring pattern 12 occurs, which is unfavorable for electrical and physiological measurements.

As described above, 12 cylindrical glass or polystyrene frames 62 with an internal diameter of 10 mm, an external diameter of 12 mm and a height of 10 mm are glued with a silicone adhesive to the pyrex glass substrate, on which 12 microelectrodes 11 in total and their wiring patterns 12 have been laid out.

These cylindrical polystyrene or glass frames 62 are fixed after aligning them each with a center of the pattern, that is a center of the 64 microelectrodes 11. The inside of these polystyrene or glass frames corresponds to a cell placement portion.

Because the method of forming the microelectrodes 11 of the multi-array 60 and the wiring pattern 12 is similar to the previously described case of the integrated multiple electrode 2, it is not described in detail.

The holders for the multi-array are two brace holders vertically sandwiching and fastening the integrated multiple electrodes, similar to the holders 3 and 4 for the integrated multiple electrode 2 (see FIGS. 1, 2, 5, 6, 7 and 8). Some alterations had to be made for the holders for the multi-array, such as concerning the dimensions of the parts that have to correspond to the position and number of the electric contact points 61 for the electrodes 11 of the multi-array 60 and their wiring patterns 12, or the number and position of the contact metal fittings 9 (see FIG. 7), but the structure for providing an electric contact for the 64×12 (768 in total) electric contact points 61 of the multi-array 60 is similar to the holders 3 and 4.

Figure 15:
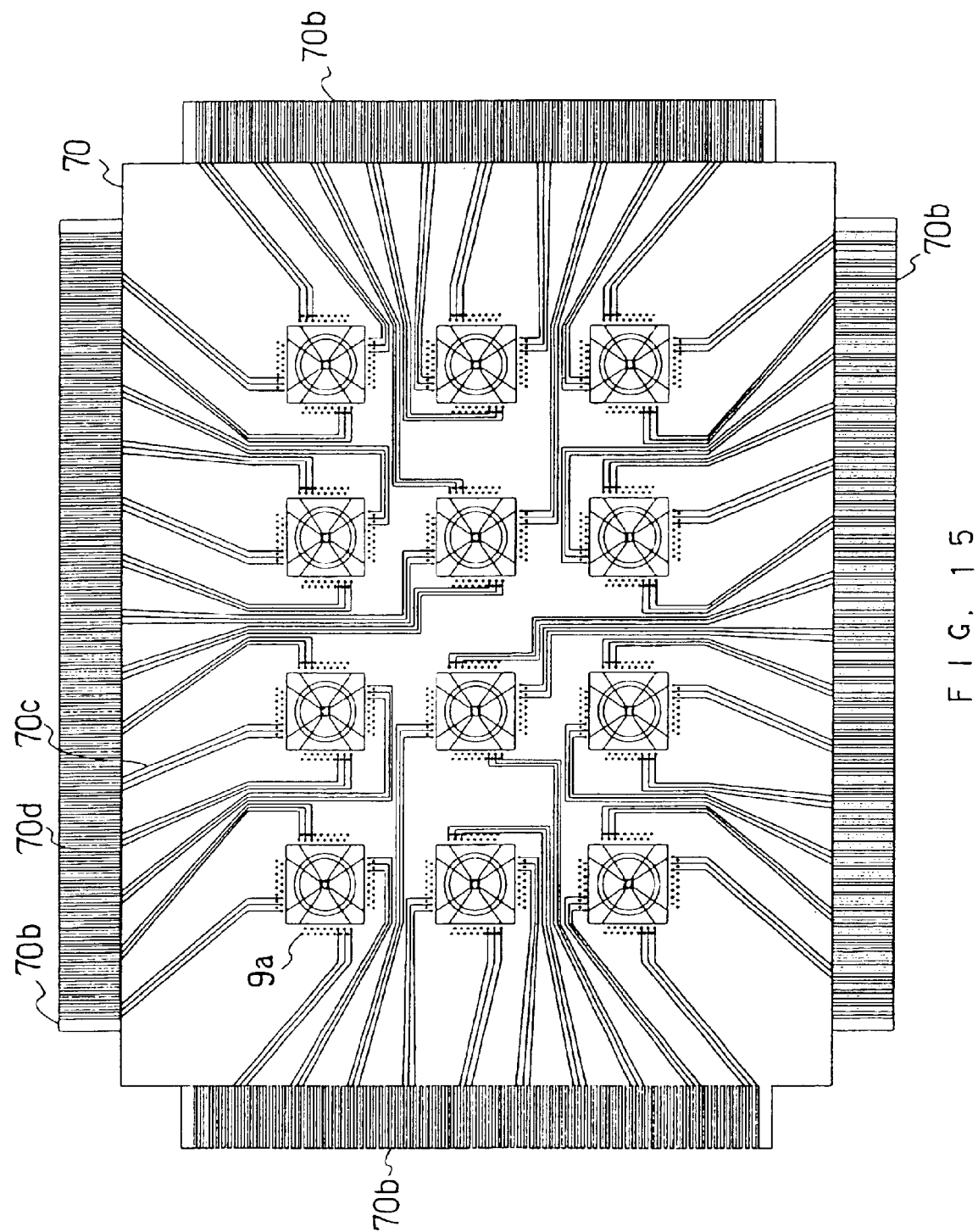
FIG. 15 is a top view showing the printed circuit board for a multi-array to which the multi-array of integrated multiple electrodes has been added.

FIG. 15 illustrates a top view of a printed circuit board 70 of the multi-array 60 (the multi-array 60 is already mounted), which fastens the multi-array 60 and the holders of the multi-array. Together with fastening the multi-array 60 and the holders of the multi-array, the multi-array printed circuit board 70 has the function of providing an electrical connection via connectors from the wiring pattern 12 reaching to the microelectrodes 11 of the multi-array, the electric contact points 61 and the contact metal fittings 9 to external parts. The method by which the multi-array 60 and the connectors for the multi-array are fastened and electrically connected by the multi-array printed circuit board 70 is similar to the method by which the integrated multiple electrode 2 and the holders 3 and 4 are fastened and electrically connected by the printed circuit board 5 (see FIG. 1, 2 and 8).

Electric contact points 70d with a 1.27 mm pitch for double sided edge connectors are formed on four edge regions 70b of the multi-array printed circuit board 70. These electric contact points 70d and the pins 9a of the contact metal fittings 9 (see FIG. 7) are connected with a wiring pattern 70c. The pins 9a are laid out in two staggered rows. The inner row is connected to the electric contact points 70d on the front surface, and the outer row is connected to the electric contact points 70d on the rear surface. (The electric contact points 70d on the rear surface are not visible in FIG. 15, because FIG. 15 is a frontal view). To lay out the wiring pattern 70c using only the front and the rear side of the multi-array printed circuit board 70 is quite a complicated task regarding the available space, because the number of electric contact points 70d is very high. Here, a printed circuit board having a multi-layered structure has been used as the multi-array printed circuit board 70. In FIG. 15, the wiring pattern 70c of a first layer is illustrated.

As is shown in this drawing, in the first layer, the wiring pattern is laid out from only a portion of the inner row of pins 9a (three pins 9a per region). If the wiring pattern is laid out from two or three pins 9a from the second layer to the sixth layer as well, then the wiring pattern 70c can be easily laid out.

Figure 16:
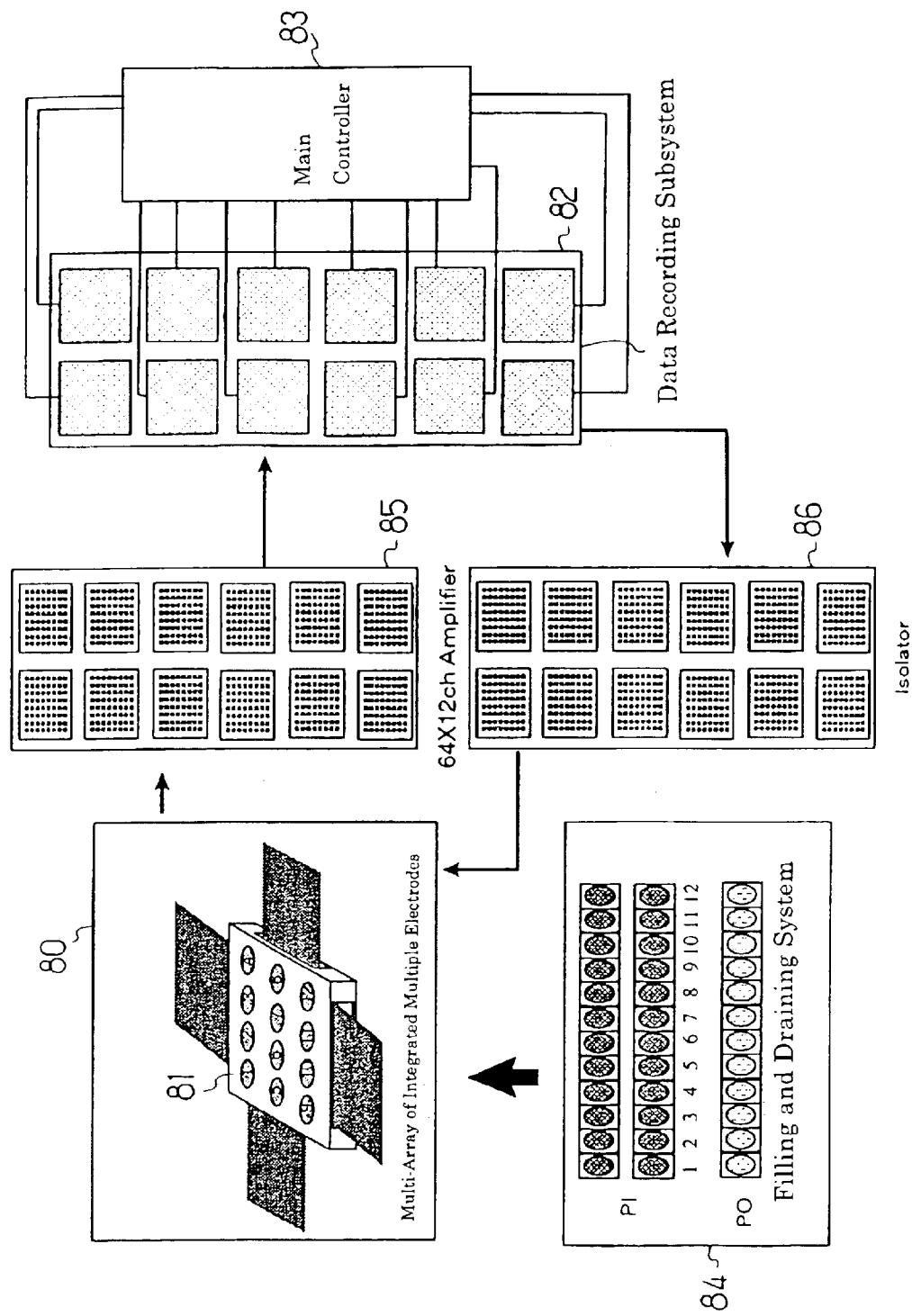
FIG. 16 is a block diagram showing an example of a device using a multi-array of integrated cell placement devices.

A preferred embodiment of a cell potential measurement device using a multi-array of integrated multiple electrodes 81 formed as described above is depicted in FIG. 16. The measurement device according to this embodiment of the present invention comprises: a multi-array of integrated multiple electrodes 81 as described above; an optical observation system comprising an inverted microscope for optically observing the cells placed on the multi-array of integrated multiple electrodes 81; a data recording sub-system 82 comprising a system for applying a stimulus signal to the cells and processing an output signal from the cells; a main controller 83 for controlling the data recording sub-system 82; a system 84 for arbitrary filling and draining of substances; an electric signal amplifying device 85 for amplifying analog-electric signals of all channels of each well (64 in the case of this embodiment); an isolator 86 for creating a stimulus electric signal from the 64 channels of each well.

Here, the data recording sub-system 82 is a device that can convert the analog electrical signal of the 64 channels employed for each well into a digital signal, perform recording and reading of the converted digital data, give out the stimulus signal of the 64 channels as an analog electric signal based on a digital signal, and consists of: a 64 channel A/D converter; a 64 channel D/A converter; a data recording device such as a magnetic disk, an optical disk or a magnetic tape; a controller for controlling the A/D converter, the D/A converter and the data recording device. It is also possible to provide the data recording sub-system 82 with a display to confirm the conditions for each operation individually. The main controller 83 administrates and controls the data recording sub-system 82 employed for the data recording of each well, performs the adjustment of all the operating conditions for the data recording sub-system 82, and displays the recorded data on an attached display.

Figure 17:
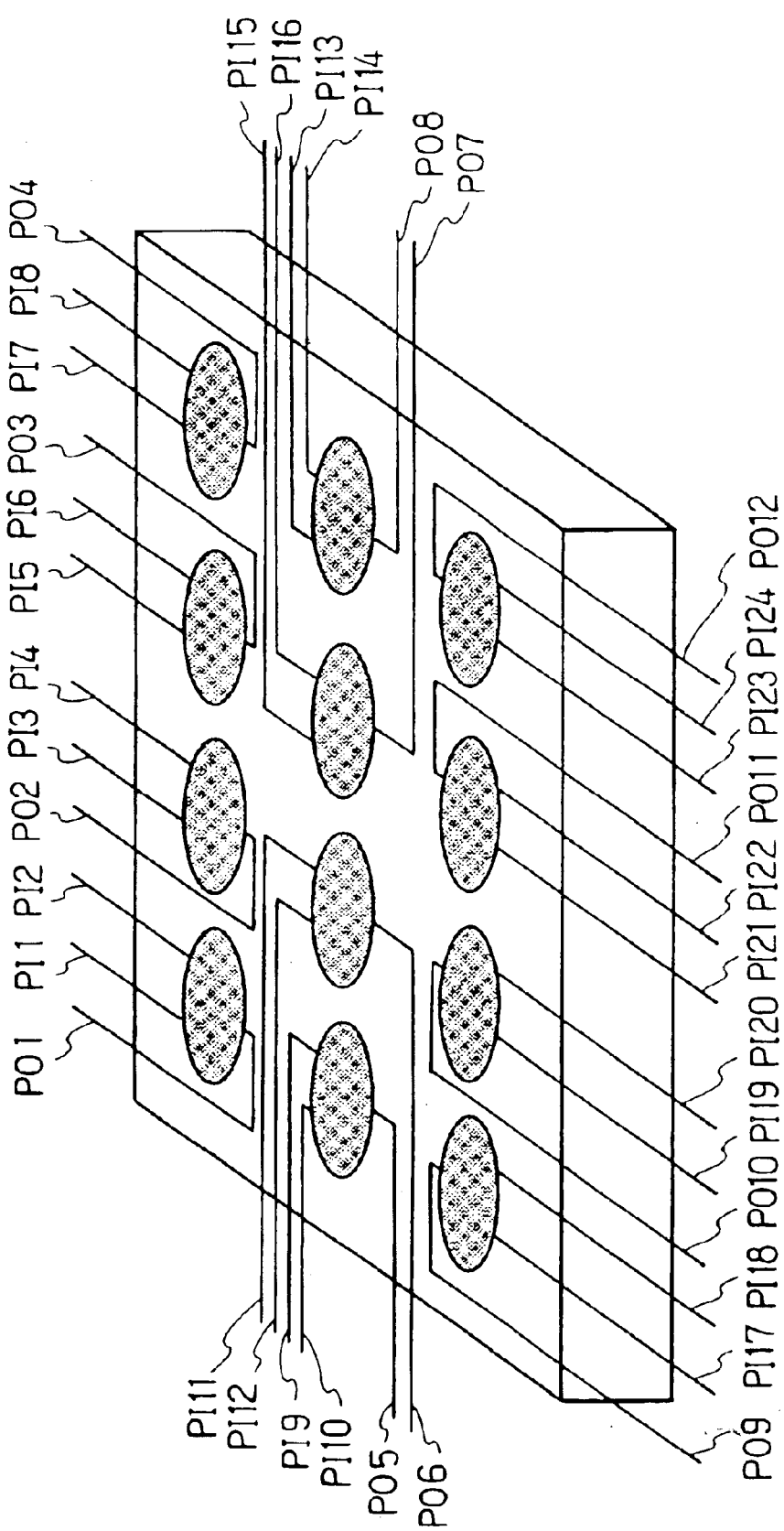
FIG. 17 is a perspective view showing the filling and draining system in a multi-array of integrated cell placement devices.

The tissue or cells, which are the test objects in each well of a multi-array of integrated multiple electrodes 81 having a set of independent electrodes in a glass or polystyrene frame as is shown in the drawing, can be cultivated for example by the culturing method explained below. Furthermore, the change of the physical and chemical environment can be performed with the filling and draining system shown in FIG. 17. This filling and draining system comprises 24 filling pumps (PI) and 12 draining pumps (PO). Two filling pumps and one draining pump are connected to each well. By installing this filling and draining system on top of the printed circuit board 70 shown in FIG. 15, an arbitrary amount of a testing fluid with an arbitrary substance concentration can be aseptically filled into each well 2, and the effect of the substance electrophysiologically tested. Furthermore, aseptical drainage is possible. Because the filling pumps are provided with valves, it is possible to fill two different fluids with each pump, so that a total of four different testing fluids can be examined. The operation of each valve and the filling rate of each pump can be controlled with the main controller 83.

Next, the operations of recording the electric signals picked up from the wells and the application of an electric stimulus signal to the wells are explained.

The main controller 83 and each data recording sub-system 82 are connected by a bidirectional bus, and the main controller 83 performs the setting, for example of data recording parameters (sampling speed, sampling time, sampling interval, sampling channel) and start/stop of the data recording individually for each data recording sub-system 82, and can send the data of the stimulus waveform to each well. The setting of these parameters can be performed individually for a single well or simultaneously for all wells together. This can be easily realized by constructing a multi-window for several wells on the setting screen for a single well. According to these settings, the data recording sub-systems 82 performs A/D conversion, data recording, and D/A conversion due to the commands from the main controller 83. The recording of electric signals from each well and the application of a stimulus waveform to each well is performed similarly as in the case of a single well. Then, because each data recording sub-system 82 resorts to the control of it's own controller, the main controller 83 is relieved of the task, and is not overtaxed even when it is in charge of controlling even more wells simultaneously. Furthermore, the data processing performed in the case of a single well can be performed similarly by the main controller 83 by sending data one by one from the data recording sub-system 82 arbitrarily designated by the main controller 83.

An example of changing the physical and chemical environment of tissue or cells cultivated on an integrated cell placement device, and measuring the change of the physical and chemical properties before and after the environmental change using a measurement device for the physical and chemical properties of tissue or cells as described above is described in the following.

EXAMPLE 1

In this example, a slice of the cerebral cortex of a rat was used as nervous tissue and cultivated with the culturing method described below. As a change in the physical and chemical environment, the stimulant drug methamphetamine has been added to the culturing fluid. Furthermore, the electrophysiological properties of the tissue or cells, that is the induced potential when a stimulus has been applied, were measured as the physical and chemical properties of the tissue or cells.

Preceding the culturing of the cells, the surface of the integrated multiple electrode 2 was covered with collagen gel not thicker than 50 $\mu$m, to promote the adhesive strength between the microelectrodes 11 of the integrated multiple electrode 2 and the cells. Then the cerebral cortex slice of the rat (not thicker than 500 $\mu$m) was placed and cultivated on top of the microelectrodes 11 and the collagen gel. FIGS. 10(*a*)–(*e*) show the measured induced potentials 30 min after methamphetamine has been added in different concentrations to the culture medium on the sixth day of culturing, and FIGS. 11(*a*)–(*c*) show the measured induced potentials 3 days after methamphetamine has been added in different concentrations to the culture medium on the third day of culturing, together with the induced potential before the addition of the methamphetamine. In other words, FIGS. 10(*a*)–(*e*) show the acute effect of the methamphetamine and FIGS. 11(*a*)–(*c*) show the chronic effect of the methamphetamine.

With regard to the acute effect (see FIG. 10), it was noted, that 0.1 mM methamphetamine has no effect on the induced potential. When 0.5 mM methamphetamine was added, the deflection of the induced potential became somewhat smaller, and after the addition of 1 mM methamphetamine, the induced potential disappeared almost completely. Then, when the methamphetamine was removed from the fluid and the culture medium was returned to its usual composition, the induced potential recovered to almost the same condition as before. FIG. 10(*a*) shows the condition before the addition of methamphetamine, FIG. 10(*b*) shows the condition when 0.1 mM methamphetamine were added, FIG. 10(*c*) shows the condition when 0.5 mM methamphetamine were added, FIG. 10(*d*) shows the condition when 1 mM methamphetamine were added, and FIG. 10(*e*) shows the condition after the methamphetamine have been removed.

Figure 11:
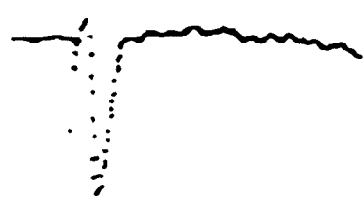
FIGS. 11(a)–(c) show the chronic effect that methamphetamine has on the induced potential of the cultivated cells, measured with a device according to the present invention.
Figure 11:
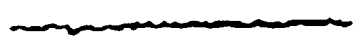
Figure 11:
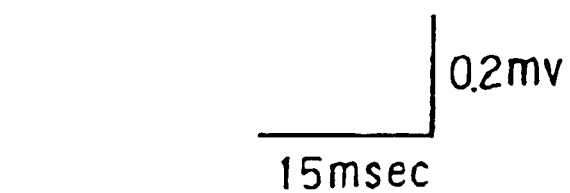

With regard to the chronic effect (see FIG. 11), it is noted, that after the addition of 0.1 mM methamphetamine, the induced potential disappeared almost completely. At this concentration the methamphetamine had no noticeable acute effect on the induced potential. Furthermore, even when the concentration was to a tenth of that value, that is 0.01 mM, then the induced potential disappeared. Moreover, even after the methamphetamine has been removed, the induced potential did not recover. FIG. 11(*a*) shows the condition before the addition of methamphetamine, FIG. 11(*b*) shows the condition when 0.01 mM methamphetamine were added, and FIG. 11(*c*) shows the condition when 0.1 mM methamphetamine were added.

Culturing Method for the Cerebal Cortex (1) Culture Medium

The following additives were added to a 1:1 mixed culture medium of Dulbecco's modified Eagle medium and a Ham F12 medium:

glucose, GIBCO 820-5023IN, 2.85 mg/L (combined with the glucose that is already contained in the above medium, this adds up to a total of 6 mg/L)

100 $\mu$M putrescine, SIGMA Co, LTD. P5780, 20 nM progesterone, SIGMA P8783, 20 nM hydrocortisone, SIGMA H0888, 20 nM sodium selenite, WAKO Co, LTD. 198-0319, 5 mg/L insulin, SIGMA 16634, 100 mg/L transferrin, SIGMA T1147, 2.438 mg/L sodium bicarbonate, 1 N HCl or 1 N NaOH, the amount suitable to attain 7.4 pH.

After adding the above additives, filtering and sterilizing it, the culture medium is preserved for use at 4° C. This composition is referred to as "culture medium" below.

(2) Structure of the Wells on the Integrated Multiple Electrode

For the sake of convenient culturing of nervous tissue or nervous cells on top of the integrated multiple electrode 2, polystyrene or glass cylinder frames 6 with an internal diameter of 22 mm an external diameter of 25 mm and a height of 10 mm have been adhered with the method described below:

(a) The necessary amount of a fluid silicon type adhesive (Dow Corning 891 or Shin-Etsu Chem. KE-42RTV) is applied to the bottom side of the polystyrene or glass cylinder 6 (internal diameter 22 mm, external diameter 25 mm, height 10 mm).

(b) The integrated multiple electrode 2 and the polystyrene or glass cylinder 6 are glued together while carefully aligning their centers.

(c) The adhesive is hardened for 24 hours in a low dust environment.

(d) After immersing the integrated multiple electrode 2 in 70% ethanol for five minutes, it is sterilized by blow-drying on a clean bench, and the surface of the integrated multiple electrode 2 is processed.

(3) Surface Processing of the Integrated Multiple Electrode 2

In order to promote the adhesive strength between the surface of the integrated multiple electrode 2 and the cells, collagen gel was applied to the surface of the integrated multiple electrode 2 in the following procedure. The following steps were carried out in a sterilized atmosphere.

(a) The following fluids A, B and C are prepared and cooled in ice water:

A. 0.3 vol % dilute hydrochloric acid collagen fluid (3.0 pH, Nitta gelatine Cellmatrix Type I-A);

B. A 1:1 mixed culture medium of Dulbecco's modified Eagle medium and a Ham F12 medium (GIBCO 30-2500EB) to which no sodium bicarbonate has been added, which is filtered and sterilized and ten times more concentrated than usual;

C. A fluid in which 100 mL of 0.05N sodium hydroxide, 2.2 g sodium bicarbonate and 4.77g HEPES (GIBCO 845-1344IM) have been dissolved, which is filtered and sterilized.

(b) While refrigerating them, the fluids A, B and C are mixed in the proportion 8:1:1. To do so, first the fluids A and B are well mixed, then added to fluid C, and then mixed again.

(c) 1 mL of the mixed fluid of (b) is poured into the well of the integrated multiple electrode 2, which has already been cooled down to a temperature of about 4° C. The fluid is spread out all over the inner surface of the well. Then, as much as possible of the mixed fluid is removed with a glass Pasteur pipette. By proceeding so, a film of the mixed fluid of not more than 50 μm thickness can be achieved.

(d) Warming the integrated multiple electrode 2 on which a mixed fluid film has been formed for 30 min at 37° C. causes gelation of the mixed fluid and production of a collagen matrix.

(e) Rinsing is performed by adding 1 mL sterile water to the well of the integrated multiple electrode 2, and removing it after about 5 min.

(f) The process step described in (e) is repeated two times (thus performed three times in total).

(g) In the well of the integrated multiple electrode 2, 1 mL of the fluid to which the additives described above (except for the insulin and the transferrin) have been added is poured to the 1:1 mixed culture medium of Dulbecco's modified Eagle medium and the Ham F12 medium (GIBCO 430-2500EB) and prepared for use by preserving it in the $CO_2$-incubator at 37° C., at least 97% rel. humidity, 5% $CO_2$ concentration and 95% air concentration.

(4) Culturing of the Nervous Tissue or Nervous Cells

The forms of culturing can be roughly separated into two kinds, namely the dispersion culturing of the nervous cells and the organic culturing of nervous tissue. Those two forms of culturing are described below.

(4-1) Dispersion Culturing Method for Visual Field Nervous Tissue of a Rat Cerebral Cortex The following process steps are all performed in a sterilized atmosphere.

(a) The brain of a 16–18 days old SD rat fetus is extracted and immersed in a Hanks' balanced salt solution (GIBCO 450-1250EB).

(b) The visual cortex is cut from the brain in the Hanks' balanced salt solution cooled with ice water, and moved into the Eagle minimum essential medium (GIBCO 410-110EB) fluid.

(c) In the Eagle minimum essential medium, the visual cortex is sliced as thinly as possible into maximally 0.2 mm squares.

(d) After being sliced, the visual cortex is put into a test tube for a centrifugal separator, and after being rinsed three times with a Hanks' balanced salt solution containing no calcium or magnesium, it is dispersed in a suitable amount of the same fluid.

(e) A Hanks' balanced salt solution containing no calcium or magnesium, in which 0.25% trypsin has been dissolved, is added to the test tube for a centrifugal separator described in (d), so that the total amount is doubled. An enzyme reaction is performed while stirring lightly and keeping the temperature constant at 37° C. for 15 min.

(f) A 10 vol. % cow fetal serum is added to the culture medium mentioned under (1-1) (including the additives; called "culture medium" below) and the result is added to the test tube for centrifugal separation mentioned under (e), so that the total amount is doubled again. Pipetting is repeated (a maximum of 20 times) with a glass Pasteur pipette, the opening diameter of which has been made smaller with a heating of the tip with a burner, and the cells are isolated.

(g) Centrifugal separation is performed at 9806.65 m/sec$^2$ (that is 1000 g) for five minutes. After the centrifugal separation, the supernatant is removed, and the precipitation is suspended in the culture medium including 5% cow fetal serum.

(h) The process step described in (g) is repeated two times (thus performed a total of three times).

(i) The finally attained precipitation is suspended in the culture medium including 5% cow fetal serum. Then, the cell concentration in the suspension is measured with a red blood corpuscle counter. After this measurement, the cell concentration is adjusted to 2–4×10$^6$/m using the same culture medium.

(j) The integrated multiple electrode that has been preserved in the $CO_2$ incubator after the processing described under (1-3) is taken from the incubator, the culture medium (not including insulin or transferrin) in the well is removed, and 500 μL culture medium comprising 5 vol. % cow fetal serum is again poured into the well. Furthermore, after the cell concentration adjustment described under (i), 100 μL cell suspension is carefully added, and the integrated multiple electrode is again put away into the $CO_2$ incubator.

(k) 3 days after the process step describe under (j), half of the culture medium is renewed. A culture medium not including cow fetal serum has been used for the renewal. By lowering the concentration of the cow fetal serum, the multiplication of cells other than the nervous cells (for example glial cells) can be controlled.

(l) The renewal of the culture medium is performed every one or two days as described above.

(4-2) Culturing Method for a Rat Cerebral Cortex Slice (a) A brain is taken from a two days old SD rat, and immersed in a Hanks' balanced salt solution cooled in iced water, with 0.25 vol. % D-glucose.

(b) In the cooled Hanks' balanced salt solution with 0.25 vol.% D-glucose, the meninges attached to the brain is removed carefully without damaging the cerebral cortex with a sharp-tipped pincette.

(c) A section is made with micro-scissors used in eye surgery, about 500 μm from the corpus callosum on one side of the cerebral cortex from which the meninges has been removed along the corpus callosum from the occipital lobe towards the frontal lobe.

(d) Next, a slice is prepared with micro-scissors used in eye surgery by cutting vertically 200–300 μm into the cerebral cortex from the sectional plane described under (c).

(e) Furthermore, the slice is adjusted with micro-scissors used in eye surgery to a size of about 1×1 mm.

(f) The integrated multiple electrode, the preparation of which has been explained under "(3) Surface Processing of the Integrated Multiple Electrode 2", is taken out of the $CO_2$ incubator, the adjusted slice of the cerebral cortex is carefully taken up without damaging it with a pipette with at least 2 mm opening diameter, and moved into the well of the integrated multiple electrode 2.

(g) The cerebral cortex is placed on the microelectrodes 11 with a layered portion pointing upwards, carefully so as not to damage the cerebral cortex, using a Pasteur pipette, the tip of which has been smoothed by heating with a burner.

(h) After the slice of the cerebral cortex has been placed on the integrated multiple electrode 2, the amount of the culture medium is adjusted so that the bottom of the slice is immersed in the culture medium and the top of the slice is in the open air.

(i) After the adjustment of the culture medium, the integrated multiple electrode 2 is placed on a Petri dish, about 5 mL of 37° C. sterile water is poured onto the Petri dish to prevent dehydration of the culture medium, and the integrated multiple electrode 2 is again placed in the $CO_2$ incubator.

(j) While observing the amount of the culture medium, the culture medium was renewed once every day. The amount of the culture medium is adjusted as described in (i).

According to this example, it was possible to examine electrically and visually to what extent methamphetamine has an effect on cells. Excellent results could be achieved concerning the screening of medicines.

EXAMPLE 2

Next, an example of a measurement not of nervous tissue but of a slice of a rat heart (tissue) is explained. This slice of a rat heart has been cultivated as explained below. The change of the spontaneous activity potential has been recorded (i) before and after the addition of acetylcholine and (ii) before and after the addition of adrenaline. The same culture medium as described in the first example was used. The structure of the integrated multiple electrode 2 and the surface processing was the same as described in the first example. In order to increase the adhesive strength between the tissue (the cells) and the microelectrodes 11 of the integrated multiple electrode 2, collagen gel (under 50 μm thick) has been applied to the surface of the integrated multiple electrode 2 before the culturing. Then the rat heart slice is placed and cultivated on the collagen gel where the microelectrodes 11 are. The rat heart slice is prepared, so that a sinoatrial node or an atrioventricular node is included.

FIGS. 12(*a*) and (*b*) show the spontaneous activity potential of the cells, before and after acetylcholine has been added to the culture medium on the fifth day of the culturing. Acetylcholine is a chemical substance that is secreted upon stimulation from the end of a parasympathic nerve in an animal body, and leads usually to a drop of blood pressure, a decrease of the heartbeat rate, a contraction of intestines, and a contraction of skeletal muscles; A can be seen in FIG. 12(*b*), after a final concentration of 1 mM acetylcholine has been added to the culture medium, the beat frequency of the spontaneous activity potential is noticeably lower than before the addition (see FIG. 12(*a*)).

FIGS. 13(*a*) and (*b*) show the spontaneous activity potential of the cells, before and after adrenaline has been added to the culture medium on the fifth day of the culturing. Adrenaline is known to increase the contraction of the heart. As can be seen in FIG. 13(*b*), after a final concentration of 1 mM adrenaline has been added to the culture medium, the beat frequency of the spontaneous activity potential is noticeably higher than before the addition (see FIG. 13(*a*)).

Below, a suitable culturing method for the heart slice is explained.

Culturing Method for the Heart Slice (1) Culture medium

The same culture medium as in example 1 was used.

(2) Formation of Wells on the Integrated Multiple Electrode 2

The same procedure as explained in example 1 applies.

(3) Surface Processing of the Integrated Multiple Electrode 2

The same surface processing as explained in example 1 was performed.

(4) Culturing Method for the Heart Slice

A similar culturing method as explained in "(4-2) Culturing Method for a Rat Cerebral Cortex Slice" of the example 1 was used. This culturing method is explained below.

(a) A heart is taken from a two days old SD rat, and immersed in a Hanks' balanced salt solution cooled with ice water, with 0.25 vol. % D-glucose. The hanks' balanced salt solution is renewed several times to rinse out the blood completely.

(b) Careful incision and preparation of a heart slice is performed, so that a sinoatrial node and an atrioventricular node are included in the heart slice.

(c) The slice is adjusted with micro-scissors used in eye surgery to a size of about 1×1 mm.

(d) The integrated multiple electrode, the preparation of which has been explained under "(3) Surface Processing of the Integrated Multiple Electrode 2", is taken out of the $CO_2$ incubator, the adjusted heart slice is carefully taken up without damaging it with a pipette with at least 2 mm opening diameter, and moved into the well of the integrated multiple electrode 2.

(e) The heart slice is placed on the microelectrodes 11, carefully as not to damage it, using a Pasteur pipette, the tip of which has been smoothed by heating with a burner.

(f) After the heart slice has been placed on the integrated multiple electrode 2, the amount of the culture medium is adjusted, so that the bottom of the slice is immersed in the culture medium and the top of the slice is in the open air.

(g) After the adjustment of the culture medium, the integrated multiple electrode 2 is placed on a Petri dish, about 5 mL of 37° C. sterile water is poured onto the Petri dish to prevent dehydration of the culture medium, and the integrated multiple electrode 2 is again placed in the $CO_2$ incubator.

(h) While observing the amount of the culture medium, the culture medium was renewed once every day. Concerning the amount of the culture medium, refer to (f).

In the examples explained above, methamphetamine, acetylcholine or adrenaline have been applied to the tissue or cells, but it is also possible to perform similar measurements using chemical substances such as fever relieving medicines, sleep inducing medicines or medicines that may have another effect, examine the change of the physical and chemical properties that these chemical substances cause in the tissue or cells, and as a result determine the effect of the chemical substance as a medication.

Possibilities for Industrial Utilization

As has been explained above, the method of testing medicines and the device for the same, and the method of measuring physical and chemical properties of tissue or cells and the device for the same according to the present invention can be advantageously used to extract only the necessary amount of the necessary tissue or cells of a living biological body, and observe the change of the physical and chemical properties of tissue or cells due to a change of the physical and chemical environment affecting the tissue or cells by suitably adjusting the physical and chemical environment. Consequently, the method of testing medicines and the device for the same, the method of measuring physical and chemical properties of tissue or cells and the device for the same according to the present invention can improve experimentation efficiency greatly, when the influence that strong electromagnetic or magnetic fields, and manmade chemical substances hitherto nonexistent in nature have on living organisms is determined. Especially, for the screening of medicines necessitating the processing of large numbers of samples, the method of testing medicines and the device for the same, and the method of measuring the physical and chemical properties of tissue or cells and the device for the same according to the present invention can be advantageously used. Moreover, with the present invention it is possible to perform an efficient screening using slices, which has been very difficult in the past, and as a result, a contribution can be made to explain functions of the nervous circuitry, or develop medicines for the cerebral nervous system. Furthermore, the present invention can make a contribution to decrease the number of animals that are used for experiments.

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description, all changes that come within the meaning and range of equivalency of the claims are intended to be embraced therein.

What is claimed is:

1. A method of testing the effect on neural or muscle tissue samples of chemical substances comprising:

providing a detector, wherein the detector comprises a plurality of microelectrodes on a substrate configured to contact the tissue sample and apply an electric stimulus to the tissue sample;

contacting said neural or muscle tissue sample with the plurality of the microelectrodes;

measuring a complete electrical waveform from the neural or muscle tissue sample;

adding said chemical substance to the neural or muscle tissue sample;

measuring the complete electrical waveform from the neural or muscle tissue sample at a time which measures response to said chemical substance; and comparing said electrical waveforms before and after said addition of said chemical substance to determine whether said added chemical substance has had an influence on the neural or muscle tissue sample.

2. The method of claim 1 for testing the effect on neural or muscle tissue samples of chemical substances as medicines, wherein the step of adding chemical substance to the neural or muscle tissue sample comprises adding said chemical substance in a selected concentration to the neural or muscle tissue sample.

3. The method of claim 1 for testing the effect on neural or muscle tissue samples of chemical substances as medicines, wherein the chronic measuring step takes place at least three days after said addition step.

* * * * *

UNITED STATES PATENT AND TRADEMARK OFFICE
CERTIFICATE OF CORRECTION

| | |
|---|---|
| PATENT NO. | : 6,890,762 B1 |
| APPLICATION NO. | : 08/913811 |
| DATED | : May 10, 2005 |
| INVENTOR(S) | : Hirokazu Sugihara et al. |

It is certified that error appears in the above-identified patent and that said Letters Patent is hereby corrected as shown below:

On the title page, item [54] and column 1, line 1,
    In the title please replace
    "METHOD FOR MEASURING PHYSIOCOCHEMICAL PROPERTIES OF TISSUES OF CELLS, METHOD FOR EXAMINING CHEMICALS, AND APPARATUS THEREFOR" with
    --METHOD FOR MEASURING PHYSICOCHEMICAL PROPERTIES OF TISSUES OR CELLS, METHOD FOR EXAMINING CHEMICALS, AND APPARATUS THEREFOR--

On the title page, item [56]:
    In the References Cited, U.S. Patent Documents section please replace
    "4,288,544 A  *  9/1981  Suzuki et al.

5,187,096 A     2/1993  Giaever et al.

5,278,048 A     1/1994  Parce et al.

5,563,067 A  *  10/1996  Sugihara et al."

with

--4,288,544 A  *  9/1981  Suzuki et al.

5,187,096  A     2/1993  Giaever et al.

5,242,806        9/1993  Yen-Maquire et al.

5,543,327        8/1996  Yen-Maquire et al.

5,563,067  A  *  10/1996  Sugihara et al.

5,643,742        7/1997  Malin et al.

5,810,725        9/1998  Sugihara et al.

6,151,519        11/2000  Sugihara et al.--

UNITED STATES PATENT AND TRADEMARK OFFICE
CERTIFICATE OF CORRECTION

PATENT NO.        : 6,890,762 B1
APPLICATION NO. : 08/913811
DATED             : May 10, 2005
INVENTOR(S)       : Hirokazu Sugihara et al.

It is certified that error appears in the above-identified patent and that said Letters Patent is hereby corrected as shown below:

In the Foreign patent Documents section please replace

"EP 0585933   3/1994

EP 0 689 051 A2 A3 12/1995

GB 1 514 046 8/1976

JP 52-31825 3/1977

JP 03-265814 11/1991

JP 6-78889 3/1994

JP 06-296595 10/1994

WO WO 90/11371 10/1990

WO WO 91/15595 Al 10/1991

WO WO 91/17240 11/1991

WO WO 92/15700 9/1992"

with

-- EP 0585933 3/1994

EP 0 689 051 A2 A3 12/1995

GB 1 514 046 8/1976

JP 52-31825 3/1977

JP 1-222767 A 6/1989

JP 03-265814 11/1991

JP 4-507199 12/1992

JP 5-506098 9/1993

UNITED STATES PATENT AND TRADEMARK OFFICE
CERTIFICATE OF CORRECTION

PATENT NO. : 6,890,762 B1
APPLICATION NO. : 08/913811
DATED : May 10, 2005
INVENTOR(S) : Hirokazu Sugihara et al.

It is certified that error appears in the above-identified patent and that said Letters Patent is hereby corrected as shown below:

In the Foreign patent Documents section please replace with (cont'd)

JP 6-78889 3/1994

JP 6-296595 A 10/1994

WO WO 90/11371 10/1990

WO WO 91/15595 Al 10/1991

WO WO 91/17240 11/1991

WO WO 92/15700 9/1992--

In the Other Publications section please add

--Hofer, E. et al., (May 1994). "Measuring Activation patterns of the Heart at a Microscopic Size Scale With Thin-Film Sensors," *J. Physiol.* 266(5 Pt 2):H2136-2145.--

Signed and Sealed this

First Day of May, 2007

JON W. DUDAS
*Director of the United States Patent and Trademark Office*